(12) United States Patent
Kelly et al.

(10) Patent No.: US 6,649,648 B1
(45) Date of Patent: Nov. 18, 2003

(54) THERAPEUTIC METHODS AND COMPOSITIONS INVOLVING ISOFLAVONES

(75) Inventors: Graham Edmund Kelly, New South Wales (AU); George Eustace Joannou, New South Wales (AU)

(73) Assignee: Novogen Research Pty Limited, North Ryde (AU)

( * ) Notice: Subject to any disclaimer, the term of this patent is extended or adjusted under 35 U.S.C. 154(b) by 0 days.

(21) Appl. No.: 09/254,026

(22) PCT Filed: Aug. 29, 1997

(86) PCT No.: PCT/AU97/00563

§ 371 (c)(1),
(2), (4) Date: Aug. 5, 1999

(87) PCT Pub. No.: WO98/08503

PCT Pub. Date: Mar. 5, 1998

(30) Foreign Application Priority Data

Aug. 30, 1996 (AU) .............................................. PO 2039

(51) Int. Cl.[7] .............................................. A61K 31/35
(52) U.S. Cl. ..................................................... 514/456
(58) Field of Search ........................................ 514/456

(56) References Cited

U.S. PATENT DOCUMENTS 4,390,559 A    6/1983   Zilliken ........................ 426/545

(List continued on next page.)

FOREIGN PATENT DOCUMENTS

AU         A-24813/97        12/1997

(List continued on next page.)

OTHER PUBLICATIONS

Adlercreutz, H. et al., "Determination of Urinary Lignans (List continued on next page.)

*Primary Examiner*—Theodore J. Criares
*Assistant Examiner*—Jennifer Kim
(74) *Attorney, Agent, or Firm*—Finnegan, Henderson, Farabow, Garrett & Dunner

(57) ABSTRACT

Therapeutic methods of treatment, compositions and foodstuffs are described which contain isoflavone compounds described by general formula (I), in which Z is H, $R_1$ is H, or $R_A CO$ where $R_A$ is $C_{1-10}$ alkyl or an amino acid, $R_2$ is H, OH, or $OR_B$ where $R_B$ is an amino acid, or $COR_A$ where $R_A$ is as previously defined, W is H, A is H or OH, and B is selected from (a), (b), (c), or W is H, and A and B taken together form a six-membered ring selected from (d), or W, A and B taken with the groups with which they are associated comprise (e), or W and A taken together with the groups with which they are associated comprise (f) and B is (g) wherein $R_3$ is H, $COR_A$ where $R_A$ is as previously defined, $CO_2R_C$ where $R_C$ is $C_{1-10}$ alkyl, or $COR_B$ where $R_B$ is as previously defined, $R_4$ is H, $COR_D$ where $R_D$ is H, OH, $C_{1-10}$ alkyl or an amino acid, $CO_2R_C$ where $R_C$ is as previously defined, $COR_E$ where $R_E$ is H, $C_{1-10}$ alkyl or an amino acid, COOH, $COR_C$ where $R_C$ is as previously defined, or $CONHR_E$ where $R_E$ is as previously defined, $R_5$ is H, $CO_2R_C$ where $R_C$ is as previously defined, or $COR_C OR_E$ where $R_C$ and $R_E$ are as previously defined, and where the two $R_5$ groups are attached to the same group they are the same or different, $R_6$ is H or hydroxy $C_{1-10}$ alkyl, X is preferably O, but may be N or S, and Y is (h) where $R_7$ is H, or $C_{1-10}$ alkyl.

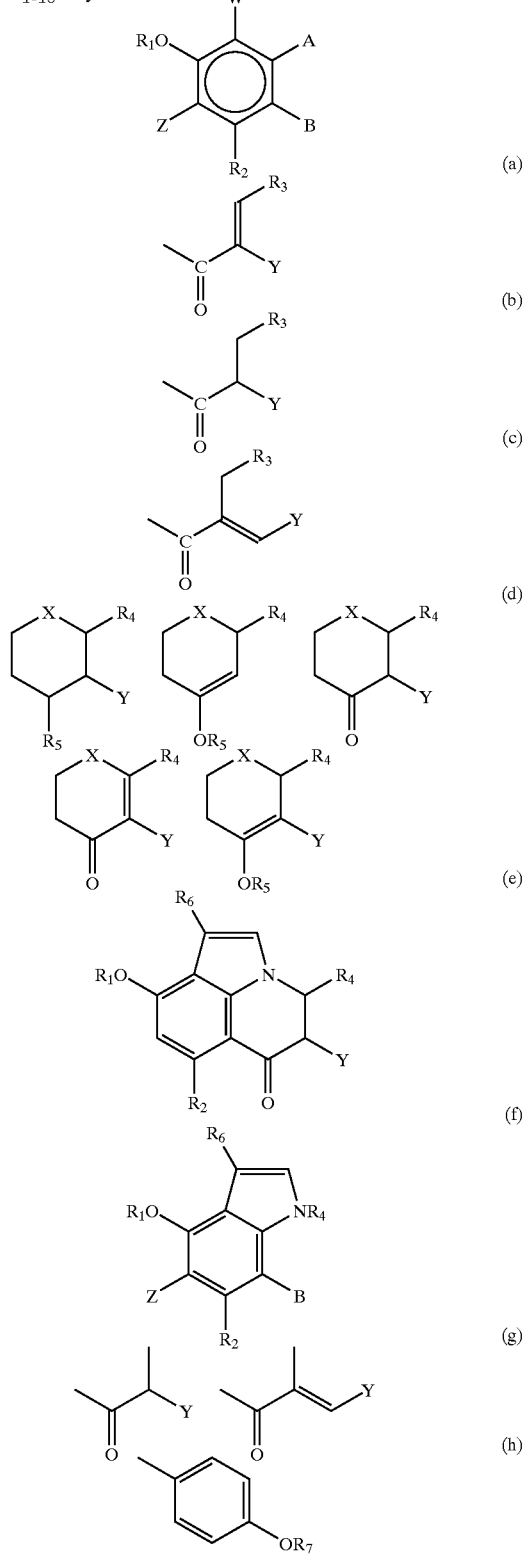

21 Claims, No Drawings

U.S. PATENT DOCUMENTS

| | | | |
|---|---|---|---|
| 5,141,746 A | 8/1992 | Fleury et al. | 424/195.1 |
| 5,352,384 A | 10/1994 | Shen | 252/398 |
| 5,424,331 A | 6/1995 | Shlyankevich | 514/456 |
| 5,523,087 A | 6/1996 | Shlyankevich | 424/195.1 |

FOREIGN PATENT DOCUMENTS

| | | |
|---|---|---|
| DE | 4432947 A1 | 3/1996 |
| EP | 0135172 | 3/1985 |
| EP | 0426998 A2 | 5/1991 |
| JP | 61246124 A | 11/1986 |
| JP | 62126186 A | 6/1987 |
| JP | 01258669 A | 10/1989 |
| JP | 02069165 A | 3/1990 |
| JP | 03047049 A | 2/1991 |
| WO | WO93/23069 | 11/1993 |
| WO | WO94/23716 | 10/1994 |
| WO | WO 96/10341 | 4/1996 |
| WO | WO 97/06273 | 2/1997 |

OTHER PUBLICATIONS and Phytoestrogen Metabolites, Potential Antiestrogens and Anticarcinogens, in Urine of Women on Various Habitual Diets," *J. Steroid Biochem*, vol. 25, No. 58, pp. 791–797 (1996).

Adlercreutz, Herman et al., "Dietary Phytoestrogens and Cancer: In Vitro and In Vivo Studies," *J. Steroid Biochem Molec. Biol.*, vol. 41, No. 3–8 pp. 331–337 (1992).

Adlercreutz, Herman et al., "Dietary phyto–oestrogens and the menopause in Japan," *The Lancet*, pp. 1233 (1992).

Adlercreutz, H. et al., "Excretion of the Ligans Enterolactone and Enterodiol and of Equol in Omnivorous and Vegetarian Postmenopausal Women and in Women with Breat Cancer," *The Lancet*, pp. 1295–1299 (1982).

Adlercreutz, H. et al., "Lignans and Phytoesrogens", *Front. gastrointest. Res.*, vol. 14, pp. 165–176 (1988).

Adlercreutz, Herman et al., "Urinary Excretion of Lignans and Isoflavonoids Phytoestrogens in Japanese Men and Women Comsuming a Tradtional Japanese Diet," *Am. J. Clin. Nutr.*, vol. 54, pp. 1093–1100 (1991).

Adlercreutz, Herman, "Western Diet and Westerm Diseases: Some Hormonal and Biochemical Mechanisms and Associations," *Scand. J. Clin. Lab. Invest, Suppl.*, vol. 201 pp. 3–23 (1990).

Anderson M.D., James et al., "Meta–Analysis of the Effects of Soy Protein Intake on Serum Lipids," *New Eng. J. Med.*, vol. 333, No. 5, pp. 276–282 (1995).

Barnes, Stephan et al., "Soybeans Inhibit Mammary Tumors in Models of Breast Cancer," *Mutagens and Carcinogens in the Diet*, pp. 239–253 (1990).

Bailey, E.T. et al., "Isoflavone Concentrations in the Leaves of the Species of the Genus Trufolium, Section Calycomorphum," *Aust. J. Agric. Res.*, vol. 22, pp. 731–736 (1971).

Bannwart, Christoph et al., "Identification of the Isoflavonic Phytoestrogen daidzein in Human Urine," *Clinica Chimica Acta*, vol. 136, pp. 165–172 (1984).

Barrow, N.J. et al., "Nutrient Potential and Capacity," *Aust. J. Agric. Res.*, vol. 17, pp. 849–861 (1996).

Barrow, N.J. et al., "Nutrient Potential and Capacity," vol. 18, pp. 55–62 (1967).

Beck, A.B., "The Oestrogenic Isoflavones of Subterranean Clover," *Aust. J. Agric. Res.*, vol. 15, pp. 223–230, (1964).

Beckham, N., "Menopause," *The Family Guide to Natural Therapies*, Greenhouse Publications, pp. 41–42, 50 (1988).

Beckham, Nancy, "Herbal Help to Avoid Menopause Symptoms," *Australian Wellbeing*, No. 29, pp. 74–76 (1988).

Beckham, Nancy, "Phyto–Oestrogens and Compounds that Affect Oestrogen Metabolism –Part I," *Aust. J. Med. Herbalism*, vol. 7, No. 1, pp. 11–16 (1995).

Beckham, Nancy, "Phyto–Oestrogens and Compounds that Affect Oestrogen Metabolism –Part II," *Aust. J. Med. Herbalism*, vol. 7, No. 2, pp. 27–33 (1995).

Bennetts, H.W. et al., "A Specific Breeding Problem of Sheep on Subterranean Clover Pastures in Western Australia," *The Australian Veterinary Journal*, vol. 22, pp. 2–12 (1946).

Beuker Valasse –Advertising Brochure –with English language translation.

Bombardelli, Ezio, "Technologies for the Processing of Medicinal Plants," in *The Medicine Plant Industry*, Chapt. 7, pp. 85–98 (1991).

Bradbury, R.B. et al., "The Chemistry of Subterranean Clover. Part I. Isolation of Formononetin and Genistein," *J. Chem. Soc.*, pp. 3447–3449 (1951).

Bradbury, R.B. et al., "Estrogens and Related Substances in Plants," in *Vitamins and Hormones Advances in Research and Applications*, Harris, R.S. et al., eds., pp. 207–233 (1954).

Brandi, M.L. "Flavonoids: biochemical effects and therapeutic applications," *Bone and Mineral*, vol. 19 (Suppl.) S3–S14 (1992).

Braden, A.W.H. et al., ¢Comparison of Plasma Phyto–Oestrogen Levels in Sheep and Cattle After Feeding on Fresh Clover," *Aust. J. Agric. Res.*, vol. 22, pp. 663–670 (1971).

Braden, A.W.H. et al., "The Oestrogenic Activity and Metabolism of Certian Isoflavones in Sheep," *Aust. J. Agric. Res.*, vol. 18 pp. 335–348 (1967).

Circle, S.J. et al., "Processing Soy Flours, Protein Concentrates and Protein Isolates," *Soybeans: Chemistry and Technology*, vol. 1, pp. 294–338 (1972).

Coward, Lori et al., "Genistein, Daidzein, and Their β–Glycoside Conjugates: Antitumor Isoflavones in Soybean Foods from American and Asian Diets," *J. Agric. Food Chem.*, vol. 41, pp. 1961–67 (1993).

Culbreth, David M.R., *A Manual of Materia Medica and Pharmacology*, pp. 19–22.

Davies, Lloyd H. et al., "Further Studies on Oestrogenic Activity in Strains of Subterranean Clober (*Trifolium Subterraneum L.*) In South–Western Australia," *Aust. J. Agric. Res.* (1965).

Davis, Harold et al., "Extraction," *Bentley's Text–Book of Pharmaceuticals*, 6th ed., XVII, pp. 272–273 (1956).

U.S. patent application Ser. No. 08/049,006, Gorbach, filed 1993.

Elridge, Arthur C., "Determination of Isoflavones in Soybean Flours, Protein Concentrates, and Isolates," *J. Agric. Food. Chem.*, vol. 30, pp. 353–355 (1982).

Elridge, A. C., "High–performance liquid chromatography separation of soybean iso–flavones and their glucosides," *J. Chrom.*, vol. 234 pp. 494–496 (1982).

Elridge, Arthur C., "Soybean Isoflavones: Effect of Environment and Variety on Composition," *J. Agric. Food Chem.*, vol. 31 pp. 394–396 (1983).

Farmakalidis, Efi et al., "Isolation of 6"–O–Acetylgenistin and 6"–O–Acetyldaidzin from Toasted Defatted Soyflakes," *J. Agric. Food. Chem.*, vol. 33, pp. 385–389 (1985).

Farmkalidis et al., Semi–Preparative High–Performance Liquid Chromatographic Isolation Soybean Isoflavones, *J. Chrom.*, vol. 295, pp. 510–514 (1984).

Farnsworth, Norman R., "Potential Value of Plants as Sources of New Antifertility Agents II," *J. Pharm. Sciences*, vol 64, No. 5, pp. 717–754 (1975).

Francis., C.M. et al., "The Distribution of Oestrogenic Insoflavones in the Genus Trifolium," *Aust. J. Agric. Res.* (1966).

Francis, C.M. et al., "Varietal Variation in the Isoflavone Content of Subterranean Clover: Its Estimation by a Microtechnique," *Aust. J. Agric. Res.* (1965).

Gildersleeve, Rhonda R. et al., "Screening Rose Clover and Subterranean Clover Germplasm for Isoflavones," *Crop. Sci.*, vol. 31 pp. 1374–1376 (1991).

Gildersleeve, Rhonda R. et al., "Detection of Isoflavones in Seedling Subterranean Clover," *Crop. Sci.*, vol. 31, pp. 889–892 (1991).

Gladstones, J.S., "Naturalized Subterranean Clover Strains in Western Australia: A Preliminary Agronomic Examination," *Aust. J. Agric. Res.*, vol. 8, pp. 713–731 (1967).

Herman, C. et al., "Soybean Phytoestrogen Intake and Cancer Risk," *American Institute of Nutrition*, pp. 757S–770S (1995).

Holt, S., "Selected Bibliography of Scientific Studies on Genistein and Other Soya Isoflavones," *Soya for Health: The Definitive Medical Guide*, pp. 159–170 (1996).

Jenkins, David J.A. et al., "Leguminous seeds in the dietary management of hyperlipidemia$^{1-3}$," *Am. J. Clin. Nut.*, vol. 38, pp. 567–573 (1983).

G. Joannou et al., "A Urinary Profile Study of Dietary Phytoestrogens. The Identification and Mode of Metabolism of New Isoflavonoids." J. Steroid Biochem. Molec. Biol. 54(3/4), pp. 167–184, Great Britian (Aug. 1995).

Jones, Amanda E. et al., "Development and Application of a High–Perfomance Liquid Chromatographic Method for the Analysis of Photoestrogens," *J. Sci. Food. Agric.*, vol. 46, pp. 357–364 (1989).

Kaldas, Rami S. et al., "Reproductive and General Metabolic Effects of Phytoestrogens in Mammals," *Reproductive Toxicology Review*, vol. 3, No. 2, pp. 81–89 (1989).

G. Kelly et al., "Metabolites of Dietary (Soya), Isoflavones in Human Urine," Clinica Chimica Acta 223, pp. 9–22 (Dec. 31, 1993).

Kitada, Yoshimi et al., "Determination of Isoflavones in soy bean by high–performance liquid chromatography with amperometric detection," *J. Chrom.*, vol. 366, pp. 403–406 (1986).

Knuckles, Benny E. et al., "Coumestrol Content of Fractions Obtained During Wet Processing of Alfalfa," *J. Agric. Food Chem.*, vol. 24, No. 6, pp. 1177–1180, (1976).

Kudou, Shigemitsu et al., "A New Isoflavone Glycoside in Soybean Seeds (Glycine max Merrill), Glycitein 7–O–β–D–(6"–O–Acetyl–Glucopyranoside," *Agric. Biol. Chem.*, vol. 55, No. 9, pp. 2227–2233 (1991).

Linder, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–333 (1967).

Lock, Margaret, "Contested meanings of the menopause," *The Lancet*, vol. 337, pp. 1270–1272 (1991).

Martin, P.M. et al., "Phytoestrogen Interaction with Estrogen Receptors in Human Breast Cancer Cells," *Endocrinology*, vol. 193, No. 5, pp. 1860–1867 (1978).

Messina, Mark et al., "The Role of Soy Products in Reducing Risk of Cancer," *J. of National Cancer Institute*, vol. 83, No. 8, pp. 541–546 (1991).

Morris, P., "Identification and Accumulation of Isoflavonoids and Isoflavone Glucosides in Soybean Leaves and Hypocotyls in Resistance Responses to Phytophthora Megasperma f.sp. Glycinea," *Physiological and Molecular Plant Pathology*, 39 pp. 221–244 (1991).

Murphy, P.A., Phytoestrogen Content of Processed Soybean Products, *Food Technology*, pp. 60–64 (1982).

Murphy, P.A., "Separation of Genistin, Daidzin and Their Aglucones, and Coumestrol by Gradient High Performance Liquid Chromatography," *J. Chrom*, vol. 211, pp. 166–169 (1991).

Naim, M. et al., "A New Isoflavone from Soya Beans," *Phytochemistry*, vol. 12, pp. 169–170 (1973).

Naim, M. et al., "Soybean Isoflavones, Characterization, Determination, and Antifungal Acitvity," *J. Agr. Food Chem.*, vol. 22, No. 5, pp. 806–810 (1974).

Nash, A.M. et al., "Fractionation and Characterization of Alcohol Extractables Associated with Soybean Proteins. Nonprotein Compounds," *J. Agr. Food Chem.*, vol. 15, No. 1, pp. 102–108 (1967).

Ohta, Naokazu et al., "Isoflavonoid Constituents of Soybeans and Isolation of a New Acetyl Daidzen," *Agric. Biol. Chem.*, 43, vol. No. 7, pp. 1415–1419 (1979).

Okano, Koji et al., "Isolation of Four Kinds of Isoflavon from Soya Bean," *Bron: Bull. Agr. Chem. Soc. Japan.* 15, vol. 15, p. 110 (1939).

Okubo, Kazuyoshi et al., "Components Responsible for the Undersirable Taste of Soybean Seeds," *Biosci. Biotech. Biochem.*, vol. 56, No. 1, pp. 90–103 (1992).

Pope, G.S., "The Importance of Pasture Plant Oestrogens in the Reproduction and Lactation of Grazing Animals," *Dairy Science Abstracts*, vol. 16, No. 5, pp. 333–356 (1954).

Price, K.R. et al., "Naturally Occurring Oestrogens in Foods–A Review," *Food Additives and Contaminants*, vol. 2, No. 2 pp. 73–106 (1985).

Reinli, Kathrin et al., "Phytoestrogen Content of Foods –A Compendium of Literature Values," *Nutrition and Cancer*, vol. 26, No. 2, pp. 123–148 (1996).

Rose, David P., "Dietary Fiber, Phytoestrogens, and Breast Cancer," *Nutrition*, vol. 8, No. 1, (1992).

Rossiter, R.C., "Physiological and Ecological Studies on the Oestrogenic Isoflavones in Subterranean Clober (T. Subterraneum L.)," *Aust. J. Agric. Res.*, Chapter III (1966).

Rossiter, R.C., "Physiological and Ecological Studies on the Oestrogenic Isoflavones in Subterranean Clober (T. Subterraneum L.)," *Aust. J. Agric. Res.*, Chapter IV (1966).

Seo, A. et al., "Improved High–Performance Liquid Chromatographic Analysis of Phenolic Acids and Isoflavonoids from Soybean Protein Products," *J. Agric. Food Chem.*, vol. 32, No. 3, pp. 530–533 (1984).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chrom.*, vol. 386 pp. 315–323 (1987).

Setchell, K.D.R. et al., "Mammalian Lignans and Photo–oestrogens Recent Studies on their Formation, Metabolism and Biological Role in Health and Disease," in Role of the Gut Flora In Toxicity and Cancer, pp. 315–339 (1988).

Setchell, KDR et al., "Nonsteroidal estrogens of dietary origin: possible roles in hormone–dependent disease," *Am. J. Clin. Nut.*, vol. 40 pp. 569–578 (1984).

Shimoyamada, Makoto et al., "Saponin Composition in Developing Soybean Seed (*Glycine max (L.) Merrill, cv. Mikuriyaao*)," Agric. Biol. Chem., vol. 55, No. 5, pp. 1403–1405 (1991).

Shutt, Donald A., "The Effects of Plant Oestrogens on Animal Reproduction," *Endeavour*, vol. 35, pp. 110–113 (1976).

Shutt, D.A. et al., "Free and Conjugated Isoflavones in the Plasma of Sheep Followed Ingestion of Oestrogenic Clover," *Aust. J. Agric. Res.*, vol. 18 pp. 647–655 (1967).

Shutt, D.A., "Interaction of Genistein With Oestradiol in the Reproductive Tract of the Ovariectomized Mouse," *J. Endocrin.*, vol. 37, pp. 231–232 (1967).

Shutt, D.A. et al., "Quantitative Aspects of Phyto–Oestrogen Metabolism in Sheep Fed on Subterranean Clover (*Trifolium Subterraneum* Cultivar Clare) or Red Clover (*Trifolium Pratense*)," *Aust. J. Agric. Res.*, vol. 21, pp. 713–722 (1970).

Shutt, D.A. et al., "The Significance of Equol in Relation to the Oestrogenic Responses in Sheep Ingesting Clover With a High Formononetin Content," *Aust. J. Agric. Res.*, vol. 19, pp. 545–553 (1968).

Shutt, D.A. et al., "Steroid and Phyto–Oestrogen Binding to Sheep Uterine Receptors In Vitro," *J. Endocr.*, vol. 52, pp. 299–310 (1972).

Smith, G.R. et al., "Influence of Harvest Date, Cultivar, and Sample Storage Method on Concentration of Isoflavones in Subterranean Clover," *Crop Science*, vol. 26, (1986).

Trease, G.E. et al., "Pharmacognosy," $12^{th}$ Ed., pp. 242–260 (1983).

Verdeal, Kathey et al., "Naturally–Occurring Estrogens in Plant Foodstuffs –A Review," *J. Food Protect.*, vol. 42, No. 7, pp. 577–583 (1979).

Walter, E.D., "Genistin (an Isoflavone Glucoside) and its Aglucone, Genistein, from Soybeans," *J. Am. Chem. Soc.*, vol. 63, pp. 3273–3276 (1941).

Walz, E., "Isoflavone–und Saponin–Glucoside in Soja hispida", *Justus Leibigs Ann. Chem.*, vol. 489, pp. 118–155 (1931).

Wang, G. et al., "A Simplified HPLC Method for Determination of Phytoestrogens in Soybean and Its Processed Products," *J. Agr. Food. Chem.*, vol. 38, No. 1, pp. 185–190 (1990).

White, Edmund et al., "Extracta," *Pharmacopedia*, 2d ed. (1909).

Wilcox, G. et al., "Oestrogenic effects of plant foods in postmenopausal women," *British Med. J.*, vol. 301, pp. 905–906 (1990).

Wong, E. et al., "Detection and Estimation of Oestrogenic Constituents in Red Clover," *J. Sci. Food Agric.*, vol. 13, pp. 304–308 (1962).

Wong, E., "The Oestrogenic Activity of Red Clover Isoflavones and Some of Their Degradation Products," *J. Endocrin.*, vol. 24, pp. 341–348 (1962).

"Estrogenic Activity in Plants," Brisbane Seminar (Summary of Talk by Nancy Beckham) (1985).

The Merck Index, Eighth Edition (1968).

"Phenolic Constituents," *Soybeans: Chemistry and Technology*, vol. 1, pp. 186–189 (1972).

"Solvent Treatment of Beans and Fractions," *Soybeans: Chemistry and Technology*, p. 149 (1972).

"Uterine Weight Changes and $^3$H–Uridine Uptake in Rats Treated with Phytoestrogens," *Can. J. Anim. Sci.*, vol. 60 pp. 531–534 (1980).

Derwent Abstract for JP 07173148 A (1995).

Derwent Abstract for JP 0517056 A (1993).

Patent Abstract of Japan for JP 61247396 (1987).

Patent Abstract of Japan for JP 62106016 (1987).

Patent Abstract of Japan for JP 62106017 (1987).

Patent Abstract of Japan for JP 0267218 (1990).

Adlercreutz, H. et al., "Determination of Urinary Lignans and Phytoestrogen Metabolites, Potential Antiestrogens and Anticarcinogens, in Urine of Women on Various Habitual Diets," *J. Steroid Biochem*, vol. 25, No. 58, pp. 791–797 (1986).

Adlercreutz, Herman et al., "Dietary Phytoestrogens and Cancer: In Vitro and In Vivo Studies," *J. Steroid Biochem Molec. Biol.*, vol. 41, No. 3–8 pp. 331–337 (1992).

Adlercreutz, Herman et al., "Dietary phyto–oestrogens and the menopause in Japan," *The Lancet*, pp. 1233 (1992).

Adlercreutz, H. et al., "Excretion of the Lignans Enterolactone and Enterodiol and of Equol in Omnivorous and Vegetarian Postmenopausal Women and in Women with Breast Cancer," *The Lancet*, pp. 1295–1299 (1982).

Adlercreutz, H. et al., "Lignans and Phytoesrogens", *Front. gastrointest. Res.*, vol. 14, pp. 165–176 (1988).

Adlercreutz, Herman et al., "Urinary Excretion of Lignans and Isoflavonoids Phytoestrogens in Japanese Men and Women Consuming a Traditional Japanese Diet," *Am. J. Clin. Nutr.*, vol. 54, pp. 1093–1100 (1991).

Adlercreutz, Herrman, "Western Diet and Wester Diseases: Some Hormonal and Biochemical Mechanisms and Associations," *Scand. J. Clin. Lab. Invest*, Suppl., vol. 201 pp. 3–23 (1990).

Anderson M.D., James et al., "Meta–Analysis of the Effects of Soy Protein Intake on Serum Lipids," *New Eng. J. Med.*, vol. 333, No. 5, pp. 276–282 (1995).

Barnes, Stephen et al., "Soybeans Inhibit Mammary Tumors in Models of Breast Cancer," *Mutagens and Carcinogens in the Diet*, pp. 239–253 (1990).

Bailey, E.T. et al., "Isoflavone Concentrations in the Leaves of the Species of the Genus Trifolium, Section Calycomorphum," Aust. J. Agric. Res., vol. 22, pp. 731–736 (1971).

Bannwart, Christoph et al., "Identification of the Isoflavonic Phytoestrogen daidzein in Human Urine," *Clinica Chimica Acta*, vol. 136, pp. 165–172 (1984).

Barrow, N.J. et al., "Nutrient Potential and Capacity," *Aust. J. Agric. Res.*, vol. 17, pp. 849–861 (1966).

Barrow, N.J. et al., "Nutrient Potential and Capacity," vol. 18, pp. 55–62 (1967).

Beck, A.B., "The Oestrogenic Isoflavones of Subterranean Clover," *Aust. J. Agric. Res.*, vol. 15, pp. 223–30, (1964).

Beckman, N., "Menopause," *The Family Guide to Natural Therapies*, Greenhouse Publications, pp. 41–42, 50 (1988).

Beckham, Nancy, "Herbal Help to Avoid Menopause Symptoms," *Australian Wellbeing*, No. 29, pp. 74–76 (1988).

Beckham, Nancy, "Phyto–Oestrogens and Compounds that Affect Oestrogen Metabolism—Part I," *Aust. J. Med. Herbalism*, vol. 7, No. 1, pp. 11–16 (1995).

Beckham, Nancy, "Phyto–Oestrogens and Compounds that Affect Oestrogen Metabolism—Part II," *Aust. J. Med. Herbalism*, vol. 7, No. 2, pp. 27–33 (1995).

Bennetts, H.W. et al., "A Specific Breeding Problem of Sheep on Subterranean Clover Pastures in Western Australia," *The Australian Veterinary Journal*, vol. 22, pp. 2–12 (1946).

Beuker Velasse—Advertising Brochure—with English language translation.

Bombardelli, Ezio, "Technologies for the Processing of Medicinal Plants," in *The Medicine Plant Industry*, Chapt. 7, pp. 85–98 (1991).

Bradbury, R.B. et al., "The Chemistry of Subterranean Clover. Part I. Isolation of Formononetin and Genistein," *J. Chem. Soc.*, pp. 3447–3449 (1951).

Bradbury, R.B. et al., "Estrogens and Related Substances in Plants," in *Vitamins and Hormones Advances in Research and Applications*, Harris, R.S. et al., eds., pp. 207–233 (1954).

Brandi, M.L., "Flavonoids: biochemical effects and therapeutic applications," *Bone and Mineral*, vol. 19 (Suppl.) S3–S14 (1992).

Braden, A.W.H. et al., "Comparison of Plasma Phyto–Oestrogen Levels in Sheep and Cattle After Feeding of Fresh Clover," *Aust. J. Agric. Res.*, vol. 22, pp. 663–670 (1971).

Braden, A.W.H. et al., "The Oestrogenic Activity and Metabolism of Certain Isoflavones in Sheep," *Aust. J. Agric. Res.*, vol. 18 pp. 335–348 (1967).

Circle, S. J. et al., "Processing Soy Flours, Protein Concentrates and Protein Isolates," *Soybeans: Chemistry and Technology*, vol. 1, pgs. 294–338 (1972).

Coward, Lori et al., "Genistein, Daidzein, and Their β–Glycoside Conjugates: Antitumor Isoflavones in Soybean Foods from American and Asian Diets," *J. Agric. Food Chem.*, vol. 41, pp. 1961–1967 (1993).

Culbreth, David M.R., *A Manual of Materia Medica and Pharmacology*, pp. 19–22.

Davies, Lloyd H. et al., "Further Studies on Oestrogenic Activity in Strains of Subterranean Clober (*Trifolium Subterraneum L.*) In South–Western Australia," *Aust. J. Agric. Res.* (1965).

Davis, Harold et al., "Extraction," *Bentley's Text–Book of Pharmaceuticals*, 6th ed., XVIII, pp. 272–273 (1956).

Düker, Eva–Maria et al., "Effects of Extracts from *Clinicifuga Racemosa* on Gonadotropin Release in Menopausal Women and Ovariectomized Rats," *Planta Med.*, vol. 57, pp. 420–424 (1991).

Eldridge, Arthur C., "Determination of Isoflavones in Soybean Flours, Protein Concentrates, and Isolates," *J. Agric. Food. Chem.*, vol. 30, pp. 353–355 (1982).

Eldridge, A.C., "High–performance liquid chromatography separation of soybean iso–flavones and their glucosides," *J. Chrom.*, vol. 234 pp. 494–496 (1982).

Eldridge, Arthur C., "Soybean Isoflavones: Effect of Environment and Variety on Composition," *J. Agric. Food Chem.*, vol. 31, pp. 394–396 (1983).

Farmakalidis, Efi et al., "Isolation of 6"–O–Acetylgenistin and 6"O–Acetyldiadzin from Toasted Defatted Soyflakes," *J. Agric. Food Chem.*, vol. 33, pp. 385–389 (1985).

Farmakalidis et al., Semi–Preparative High–Performance Liquid Chromatographic Isolation Soybean Isoflavones, *J. Chrom.*, vol. 295, pp. 510–514 (1984).

Farnsworth, Norman R., "Potenial Value of Plants as Sources of New Antifertility Agents II," *J. Pharm. Sciences*, vol. 64, No. 5, pp. 717–754 (1975) Structures.

Francis., C.M. et al., "The Distribution of Oestrogenic Isoflavones in the Genus Trifolium," *Aust. J. Agric. Res.* (1966).

Francis, C.M. et al., "Varietal Variation in the Isoflavone Content of Subterranean Clover: Its Estimation by a Microtechnique," *Aust. J. Agric. Res.* (1965).

Gildersleeve, Rhonda R. et al., "Screening Rose Clover and Subterranean Clover Germplasm for Isoflavone," *Crop. Sci.*, vol. 31, pp. 1374–1376 (1991).

Gildersleeve, Rhonda R. et al., "Detection of Isoflavones in Seedling Subterranean Clover," *Crop Sci.*, vol. 31, pp. 889–892 (1991).

Gladstones, J.S., "Naturalized Subterranean Clover Strains in Western Australia: A Preliminary Agronomic Examination," *Aust. J. Agric. Res.*, vol. 8, pp. 713–731 (1967).

Herman, C. et al., "Soybean Phytoestrogen Intake and Cancer Risk," *American Institute of Nutrition*, pp. 7575–7705 (1995) cancer.

Holt, S., "Selected Bibliography of Scientific Studies on Genistein and Other Soya Isoflavones," *Soya for Health: The Definitive Medical Guide*, pp. 159–170 (1996).

Jenkins, David J.A. et al., "Leguminous seeds in the dietary management of hyperlipidemia$^{1-3}$," *Am. J. Clin. Nut.*, vol. 38, pp. 567–573 (1983).

G. Joannou et al., "A Urinary Profile Study of Dietary Phytoestrogens. The Identification and Mode of Metabolism of New Isoflavonoids." J. Steroid Biochem. Molec. Biol. 54 (3/4), pp. 167–184, Great Britain (Aug. 1995). (Structures).

Jones, Amanda E. et al., "Development and Application of a High–Performance Liquid Chromatographic Method for the Analysis of Phytoestrogens," *J. Sci. Food Agric.*, vol. 46, pp. 357–364 (1989).

Kaldas, Rami S. et al., "Rami S. et al., "Reproductive and General Metabolic Effects of Phytoestrogens in Mammals," *Reproductive Toxicology Review*," vol. 3, No. 2, pp. 81–89 (1989).

G. Kelly et al., "Metabolites of Dietary (Soya), Isoflavones in Human Urine," Clinica Chimica Acta 223, pp. 9–22 (Dec. 31, 1993).

Kitada, Yoshimi et al., "Determination of Isoflavones in soy bean by high–performance liquid chromatography with amperometric detection," *J. Chrom.*, vol. 366, pp. 403–406 (1986).

Knuckles, Benny E. et al., "Coumestrol Content of Fractions Obtained During Wet Processing of Alfalfa," *J. Agric. Food Chem.*, vol. 24, No. 6, pp. 1177–1180, (1976).

Kudo, Shigemitsu et al., "A New Isoflavone Glycoside in Soybean Seeds (Glycine max Merrill), Glycitein 7–O–β–D(6"–O–Acetyl)–Glucopyranoside," *Agric. Biol. Chem.*, vol. 55, No. 3, pp. 859–860 (1991).

Kudo, Shigemitsu et al., "Malonyl Isoflavone Glycosides in Soybean Seeds (*Glycine max* Merrill)," *Agric. Biol. Chem.*, vol. 55, No. 9, pp. 2227–2233 (1991).

Lindner, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–333 (1967).

Lock, Margaret, "Contested meanings of the menopause," *The Lancet*, vol. 337, pp. 1270–1272 (1991).

Martin, P.M. et al., "Phytoestrogen Interaction with Estrogen Receptors in Human Breast Cancer Cells," *Endocrinology*, vol. 193, No. 5, pp. 1860–1867 (1978).

Messina, Mark et al., "The Role of Soy Products in Reducing Risk of Cancer," *J. of National Cancer Institute,* vol. 83, No. 8, pp. 541–546 (1991).

Morris, P., "Identification and Accumulation of Isoflavonoids and Isoflavone Glucosides in Soybean Leaves and Hypocotyls in Resistance Responses to Phytophthora Megasperma f.sp. Glycinea," *Physiological and Molecular Plant Pathology,* 39 pp. 221–244 (1991).

Murphy, P.A., Phytoestrogen Content of Processed Soybean Products, *Food Technology,* pp. 60–64 (1982).

Murphy, P.A., "Separation of Genistin, Daidzin and Their Aglucones, and Coumesterol by Gradient High Performance Liquid Chromatography," *J. Chrom,* vol. 211, pp. 166–169 (1991).

Naim, M. et al., "A New Isoflavone from Soya Beans," *Phytochemistry,* vol. 12, pp. 169–170 (1973).

Naim, M. et al., "Soybean Isoflavones, Characterization, Determination, and Antifungal Activity," *J. Agr. Food Chem.,* vol. 22, No. 5, pp. 806–810 (1974).

Nash, A.M. et al., "Fractionation and Characterization of Alcohol Extractables Associated with Soybean Proteins. Nonprotein Components," *J. Agr. Food Chem.,* vol. 15, No. 1, pp. 102–108 (1967).

Ohta, Naokazu et al., "Isoflavonoid Constituents of Soybeans and Isolation of a New Acetyl Daidzin," *Agric. Biol. Chem.,* 43, Vol. No. 7, pp. 1415–1419 (1979).

Okano, Koji et al., "Isolation of Four Kinds of Isoflavon from Soya Bean," *Bron: Bull. Agr. Chem. Soc. Japan.* 15, vol. 15, p. 110 (1939).

Okubo, Kazuyoshi et al., "Components Responsible for the Undersirable Taste of Soybean Seeds," *Biosci. Biotech. Biochem.,* vol. 56, No. 1, pp. 99–103 (1992).

Pope, G.S., "The Importance of Pasture Plant Oestrogens in the Reproduction and Lactation of Grazing Animals," *Dairy Science Abstracts,* vol. 16, No. 5, pp. 333–356 (1954).

Price, K.R. et al., "Naturally Occurring Oestrogens in Foods—A Review," *Food Additives and Contaminants,* vol. 2, No. 2 pp. 73–106 (1985).

Reinli, Kathrin et al., "Phytoestrogen Content of Foods—A Compendium of Literature Values," *Nutrition and Cancer,* vol. 26, No. 2, pp. 123–148 (1996).

Rose, David P., "Dietary Fiber, Phytoestrogens, and Breast Cancer," *Nutrition,* vol. 8, No. 1 (1992).

Rossiter, R.C., "Physiological and Ecological Studies on the Oestrogenic Isoflavones in Subterranean Clober (T. Subterraneum L.)," *Aust. J. Agric. Res.,* Chapter III (1966).

Rossiter, R.C., "Physiological and Ecological Studies on the Oestrogenic Isoflavones in Subterranean Clober (T. Subterraneum L.)," *Aust. J. Agric. Res.,* Chapter IV (1966).

Seo, A. et al., "Improved High–Performance Liquid Chromatographic Analysis of Phenolic Acids and Isoflavonoids from Soybean Protein Products," *J. Agric. Food Chem.,* vol. 32, No. 3, pp. 530–533 (1984).

Setchell, K.D.R. et al.,"High–Performance Liquid Chromatographic Analysis of Phytoestrogens in Soy Protein Preparations with Ultraviolet, Electrochemical and Thermospray Mass Spectrometric Detection," *J. Chrom.,* vol. 386 pp. 315–323 (1987).

Setchell, K.D.R. et al., "Mammalian Lignans and Phyto–estrogens Recent Studies on their Formation, Metabolism and Biological Role in Health and Disease," in Role of the Gut Flora In Toxicity and Cancer, pp. 315–339 (1988).

Setchell, KDR et al., "Nonsteroidal estrogens of dietary origin: possible roles in hormone–dependent disease," *Am. J. Clin. Nut.,* vol. 40 pp. 569–578 (1984).

Shimoyamada, Makoto et al., "Saponin Composition in Developing Soybean Seed (*Glycine max*(L.) Merrill, cv. *Mikuriyaao*)," *Agric. Biol. Chem.,* vol. 55, No. 5, pp. 1403–1405 (1991).

Shutt, Donald A., "The Effects of Plant Oestrogens on Animal Reproduction," *Endeavour,* vol. 35, pp. 110–113 (1976).

Shutt, D.A. et al., "Free and Conjugated Isoflavones in the Plasma of Sheep Followed by Ingestion of Oestrogenic Clover," *Aust. J. Agric. Res.,* vol. 18 pp. 647–655 (1967).

Shutt, D.A. "Interaction of Genistein With Oestradiol in the Reproductive Tract of the Ovariectomized Mouse," *J. Endrocrin.,* vol. 37, pp. 231–232 (1967).

Shutt, D.A. et al., "Quantitative Aspects of Phyto-=Oestrogen Metabolism in Sheep Fed on Subterranean Clover (*Trifolium Subterraneum* Cultivar Clare) or Red Clover (*Trifolium Pratense*)," *Aust. J. Agric. Res.,* vol. 21, pp. 713–722 (1970).

Shutt, D.A. et al., "The Significance of Equol in Relation to the Oestrogenic Responses in Sheep Ingesting Clover With a High Formononetin Content," *Aust. J. Agric. Res.,* vol. 19, pp. 545–553 (1968).

Shutt, D.A. et al., "Steroid and Phyto–Oestrogen Binding to Sheep Uterine Receptors In Vitro," *J. Endocr.,* vol. 52, pp. 299–310 (1972).

Smith, G.R. et al., "Influence of Harvest Date, Cultivar, and Sample Storage Method on Concentration of Isoflavones in Subterranean Clover," *Crop Science,* vol. 26 (1986).

Trease, G.E. et al., "Pharmacognosy," $12^{th}$ Ed., pp. 242–260 (1983).

Verdeal, Kathey et al., "Naturally–Occurring Estrogens in Plant Foodstuffs—A Review," *J. Food Protect.,* vol. 42, No. 7, pp. 577–583 (1979).

Walter, E.D., "Genistin (an Isoflavone Glucoside) and its Aglucone, Genistein, from Soybeans," *J. Am. Chem. Soc.,* vol. 63, pp. 3273–3276 (1941).

Walz, E., "Isoflavon– und Saponin–Glucoside in Soja hispida", *Justus Liebigs Ann. Chem.,* vol. 489, pp. 118–155 (1931).

Wang, G. et al., "A Simplified HPLC Method for Determination of Phytoestrogens in Soybean and Its Processed Products," *J. Agr. Food Chem.,* vol. 38, No. 1, pp. 185–190 (1990).

White, Edmund et al., "Extracta," *Pharmacopedia,* 2d ed. (1909).

Wilcox, G. et al., "Oestrogenic effects of plant foods in postmenopausal women," *British Med. J.,* vol. 301, pp. 905–906 (1990).

Wong, E. et al., "Detection and Estimation of Oestrogenic Constituents in Red Clover," *J. Sci. Food Agric.,* vol. 13, pp. 304–308 (1962).

Wong, E., "The Oestrogenic Activity of Red Clover Isoflavones and Some of Their Degradation Products," *J. Endocrin.,* vol. 24, pp. 341–348 (1962).

"Estrogenic Activity in Plants," Brisbane Seminar (Summary of Talk by Nancy Beckham) (1985).

The Merck Index, Eighth Edition (1968).

"Phenolic Constituents," *Soybeans: Chemistry and Technology,* vol. 1, pp. 186–189 (1972).

"Solvent Treatment of Beans and Fractions," *Soybeans: Chemistry and Technology,* p. 149 (1972).

"Uterine Weight Changes and $^3$H–Uridine Uptake in Rats Treated with Phytoestrogens," *Can. J. Anim. Sci.,* vol. 60 pp. 531–534 (1980).
Derwent Abstract for JP 07173148 A. (1995).
Derwent Abstract for JP 0517056 A. (1993).
Patent Abstract of Japan for JP 61247396. (1987).
Patent Abstract of Japan for JP 62106016. (1987).
Patent Abstract of Japan for JP 62106017. (1987).
Patent Abstract of Japan for JP 0267218. (1990).
Düker, Eva–Maria et al., "Effects of Extracts from Clinicifuga Racemosa on Gonadotropin Release in Menopausal Women and Ovariectomized Rats," *Planta Med.,* vol. 57, pp. 420–424 (1991).
Kudou, Shigemitsu et al., "Malonyl Isoflavone Glycosides in Soybean Seeds (Glycine max Merrill)," *Agric. Biol. Chem.,* vol. 55, No. 9, pp. 2227–2233 (1991).

THERAPEUTIC METHODS AND COMPOSITIONS INVOLVING ISOFLAVONES

This invention relates to therapeutic uses, methods, compounds, formulations, drinks and food stuffs involving, containing, comprising and/or including certain isoflavone compounds.

The isoflavone compounds according to this invention are described by general formula I, (I)

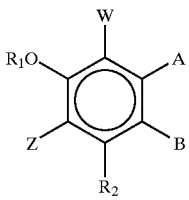

in which
Z is H,
$R_1$ is H, or $R_A CO$ where $R_A$ is $C_{1-10}$ alkyl or an amino acid,
$R_2$ is H, OH, or $OR_B$ where $R_B$ is an amino acid or $COR_A$ where $R_A$ is as previously defined, W is H, A is H or OH, and B is selected from

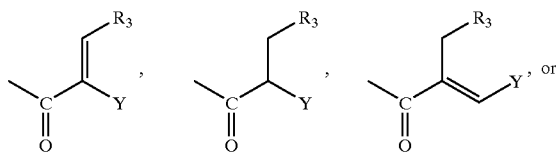

W is H, and A and B taken together form a six membered ring selected from

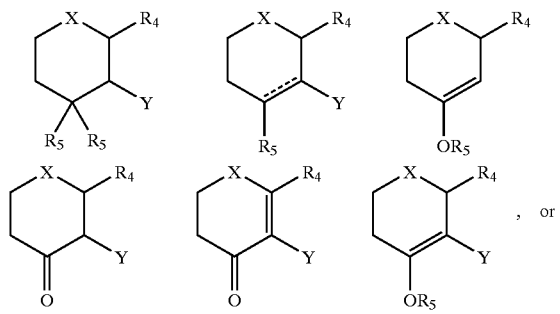

W, A and B taken with the groups with which they are associated comprise

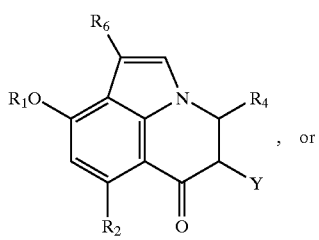

W and A taken together with the groups with which they are associated comprise

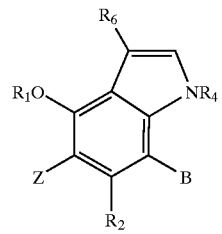

and B is

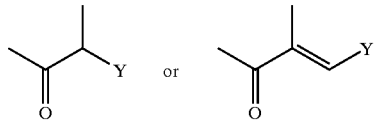

wherein
$R_3$ is H, $COR_A$ where $R_A$ is as previously defined, $CO_2R_C$ where $R_C$ is $C_{1-10}$ alkyl, or $COR_B$ where $R_B$ is as previously defined,
$R_4$ is H, $COR_D$ where $R_D$ is H, OH, $C_{1-10}$ alkyl or an amino acid, $CO_2R_C$ where $R_C$ is as previously defined, $COR_E$ where $R_E$ is H, $C_{1-10}$ alkyl or an amino acid, COOH, $COR_C$ where $R_C$ is as previously defined, or $CONHR_E$ where $R_E$ is as previously defined,
$R_5$ is H, $CO_2R_C$ where $R_C$ is as previously defined, or $COR_COR_E$ where $R_C$ and $R_E$ are as previously defined, and where the two $R_5$ groups are attached to the same group they are the same or different,
$R_6$ is H or hydroxy $C_{1-10}$ alkyl,
X is preferably O, but may be N or S, and
Y is

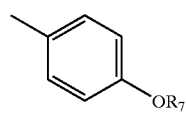

where $R_7$ is H, or $C_{1-10}$ alkyl.
provided that compounds of the formula I where
$R^1$, W and Z are H
$R^2$ is H or OH
A and B taken together are a six membered ring

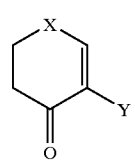

Y is as defined above
and $R^7$ is H or $OCH_3$,
are specifically excluded, and
provided that where the method is a method for the treatment or prophylaxis of menopausal syndrome or premenstrual tension syndrome compounds of the formula I where
$R^1$ is H, W and Z are H, and $R_2$ is H or OH, A and B taken together are a six membered ring

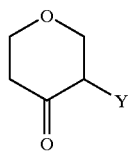

or A is OH and B is

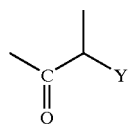

where Y is as defined above and $R_7$ is H are specifically excluded, and further provided that where the method is a method for the treatment of a form of cancer or rheumatoid arthritis compounds of the formula I where:

$R_1$ and W are H, Z is H or $OCH_3$ and $R_2$ is H or OH, and A and B taken together are a six membered ring of the formula

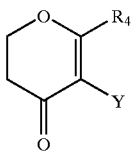

Y is as defined above, $R_4$ is $CO_2H$ or $CO_2CH_2CH_3$, and $R_7$ is H are specifically excluded.

Preferably the compounds of the formula I are selected from:

(1)
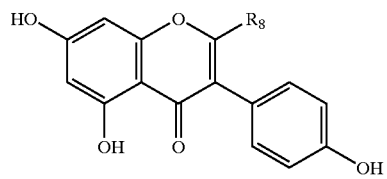

(2)
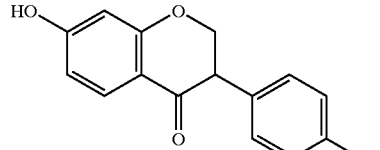

(3)
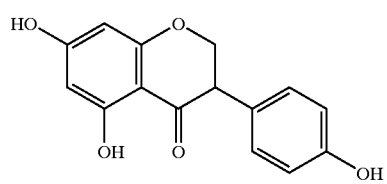

(4)
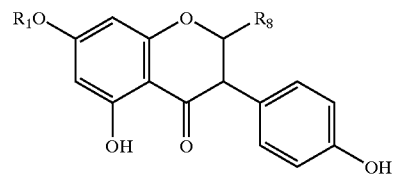

(5)
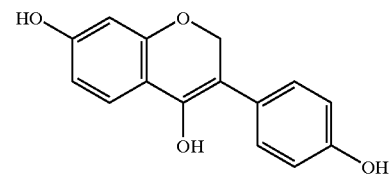

(6)
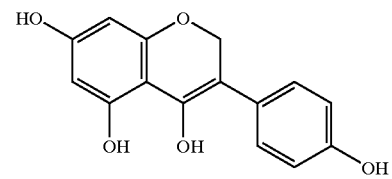

(7)
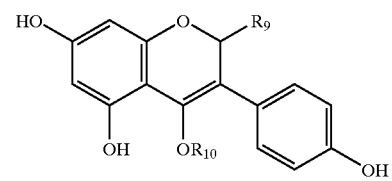

(8)
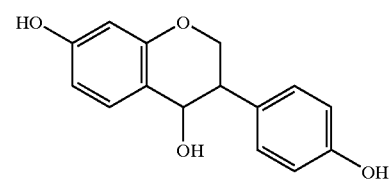

(9)
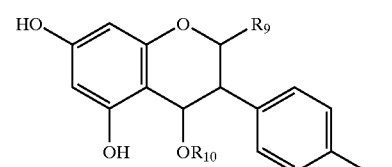

(10)
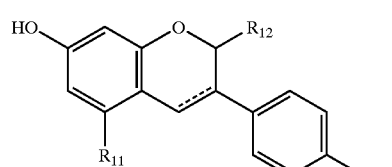

(11)
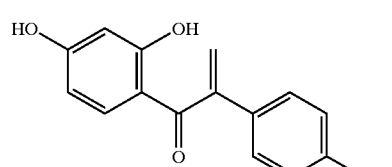

(12)
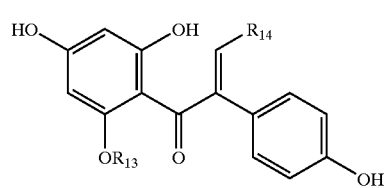

-continued

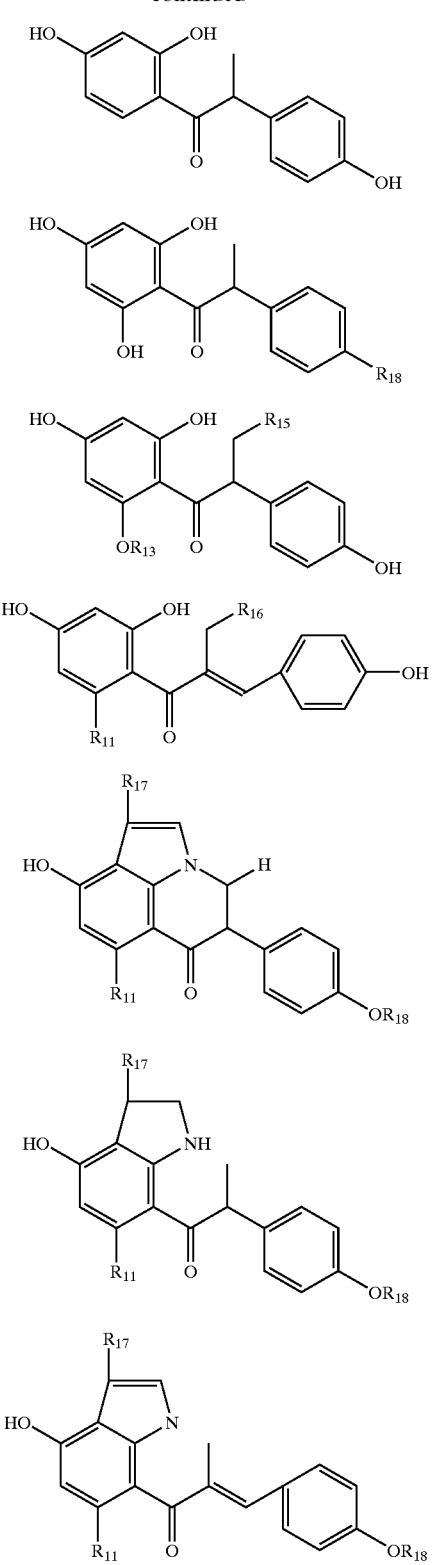

wherein
$R_8$ is COR where $R_D$ is as previously defined,
$R_9CO_2R_C$ or $COR_E$ where $R_C$ and $R_E$ are as previously defined,
$R_{10}$ is $COR_C$ or $COR_COR_E$ where $R_C$ and $R_E$ are as previously defined,
$R_{11}$ is H or OH,
$R_{12}$ is H, COOH, $CO_2R_C$ where $R_C$ and is as previously defined, or $CONHR_E$ where $R_E$ is as previously defined,
$R_{13}$ is OH, $OR_B$ where $R_B$ is as previously defined, or $COR_A$ where $R_A$ is as previously defined,
$R_{14}$ is H, or $COR_A$ where $R_A$ is as previously defined,
$R_{15}$ is $COR_A$ where $R_A$ is as previously defined,
$R_{16}$ is H, $COR_B$ or $CO_2R_C$ where $R_B$ and $R_C$ are as previously defined,
$R_{17}$ is H or hydroxy $C_{1-10}$ alkyl,
$R_{18}$ is H or $C_{1-10}$ alkyl,
and "---" represents either a single bond or a double bond.

Alkyl groups may be straight or branched chains. $C_{1-10}$ alkyl preferably contains from 1 to 5 carbons, more preferably methyl, ethyl or propyl.

Certain of the above compounds may be referred to by the names dihydrodaidzein (compound 1 where $R_8$ is H), dihydrogenestein (compounds 2 and 5), dehydro-O-desmethylangolensin (compound 11), tetrahydrodaidzein (compound 8), equol and dehydroequol (compound 10), O-desmethyl-angolensin (ODMA—compound 13), and 6-hydroxy-O-desmethylangolensin (6-hydroxy-ODMA—compound 14).

It has surprisingly been found by the inventors that compounds of the formula I, and more specifically compounds of the formulae 1 to 19 have particular utility and effectiveness in the treatment, prophylaxis, amelioration defence against, and/or prevention of menopausal syndrome including hot flushes, anxiety, and depression, mood swings, night sweats, headaches, and urinary incontinence; osteoporosis; premenstrual syndrome, including fluid retention, cyclical mastalgia, and dysmenorrhoea; Reynaud's Syndrome; Reynaud's Phenomenon; Buergers Disease; coronary artery spasm; migraine headaches; hypertension; benign prostatic hypertrophy; breast cancer; uterine cancer; ovarian cancer; testicular cancer; large bowel cancer; endometrial cancer; prostatic cancer uterine cancer; atherosclerosis; Alzheimers disease; inflammatory diseases including inflammatory bowel disease, ulcerative colitis, Crohns disease; rheumatic diseases including rheumatoid arthritis; acne; baldness including male pattern baldness (alopecia hereditaria); psoriasis and diseases associated with oxidant stress including cancer, myocardial infarction stroke, arthritis, sunlight induced skin damage or cataracts.

According to a first aspect of the present invention there is provided a method for the treatment, prophylaxis, amelioration, defence against, and/or prevention of menopausal syndrome including hot flushes, anxiety, and depression, mood swings, night sweats, headaches, and urinary incontinence; osteoporosis; premenstrual syndrome, including fluid retention, cyclical mastalgia, and dysmenorrhoea; Reynaud's Syndrome; Reynaud's Phenomenon; Buergers Disease; coronary artery spasm; migraine headaches; hypertension; benign prostatic hypertrophy; breast cancer; uterine cancer; ovarian cancer; testicular cancer; large bowel cancer; endometrial cancer; prostatic cancer; uterine cancer; atherosclerosis; Alzheimers disease; inflammatory diseases including inflammatory bowel disease, ulcerative colitis, Crohns disease; rheumatic diseases including rheumatoid arthritis; acne; baldness including male pattern baldness (alopecia hereditaria); psoriasis and diseases associated with oxidant stress including cancer, myocardial infarction stroke, arthritis, sunlight induced skin damage or cataracts which comprises administering to a subject a therapeutically effective amount of one or more compounds of the formula I:

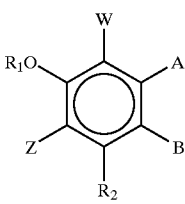

(I)

where $R_1$, $R_2$, Z, W, A and B are as previously defined, either alone or in association with one or more pharmaceutically acceptable carriers and/or excipients.

Preferably, one or more compounds of the formulae 1 to 19 may be used in the treatment, prophylaxis, amelioration of menopausal syndrome including hot flushes, anxiety, and depression, mood swings, night sweats, headaches, and urinary incontinence; osteoporosis; premenstnial syndrome, including fluid retention, cyclical mastalgia, and dysmenorrhoea; Reynaud's Syndrome; Reynaud's Phenomenon; Buergers Disease; coronary artery spasm; migraine headaches; hypertension; benign prostatic hypertrophy; breast cancer; uterine cancer; ovarian cancer; testicular cancer; large bowel cancer; endometrial cancer; prostatic cancer; uterine cancer; atherosclerosis; Alzheimers disease; inflammatory diseases including inflammatory bowel disease, ulcerative colitis, Crohns disease; rheumatic diseases including rheumatoid arthritis; acne; baldness including male pattern baldness (alopecia hereditaria); psoriasis and diseases associated with oxidant stress including cancer, myocardial infarction stroke, arthritis, sunlight induced skin damage or cataracts (for convenience hereafter referred to as the "therapeutic indications"). Cancer, myocardial infarction, stroke, arthritis, sunlight induced skin damage and cataracts are generally regarded to be associated with oxidant stress. This invention includes the treatment of diseases associated with oxidant stress.

A second aspect of the present invention is the use of compounds of the formula I for the manufacture of a medicament for the treatment, amelioration, defence against, prophylaxis and/or prevention of one or more of the therapeutic indications. It is particularly preferred that one or more compounds of the formulae 1 to 19 are employed in the treatment, prophylaxis, amelioration, defence against, and/or prevention of said indications.

A third aspect of the present invention is use of one or more compounds of the formula I in the treatment, amelioration, defence against, prophylaxis and/or prevention of one or more of the therapeutic indications. Compounds of the formulae 1 to 19 are particularly preferred.

A fourth aspect of the present invention comprises an agent for the treatment, prophylaxis, amelioration, defence against and/or treatment of the therapeutic indications which comprises one or more compounds of the formula I either alone or in association with one or more carriers or excipients. Compounds of the formulae 1 to 19 are particularly preferred.

A fifth aspect of the invention is a therapeutic composition which comprises one or more compounds of the formula I in association with one or more pharmaceutical carriers and/or excipients. It is preferred that the compositions comprise one or more compounds of the formulae 1 to 19.

A sixth aspect of the present invention is a drink or food-stuff, which contains one or more compounds of the formula I. Preferably the food stuff contains one or more compounds of the formulae 1 to 19.

A seventh aspect of the present invention is a microbial culture or a food-stuff containing one or more microbial strains which microorganisms produce one or more compounds of the formula I. Preferably said microorganisms produce one or more of the compounds of the formulae 1 to 19.

An eighth aspect of the present invention relates to one or more microorganisms which produce one or more compounds of the formula I. Preferably the microorganism is a purified culture, which may be admixed and/or administered with one or more other cultures which produce compounds of the formula I. The compounds of the formula I preferably are selected from one or more of compounds of the formulae 1 to 19.

In a further aspect this invention is directed to compounds of the formula I. Preferably said compounds comprise compounds of the formulae 1 to 19.

Compounds of the present invention have particular application in the treatment of diseases associated with or resulting from estrogenic effects androgenic effects, vasolidatory and spasmodic effects, inflammatory effects and oxidative effects.

The amount of the compound of the formula I which is required in a therapeutic treatment according to the invention will depend upon a number of factors, which include the specific application, the nature of the particular compound used, the condition being treated, the mode of administration and the condition of the patient. In general, a daily dose per patient is in the range of 0.1 mg to 2 g; typically from 0.5 mg to 1 g; preferably from 50 mg to 200 mg.

Compounds of the formula I may be in a manner and amount as is conventionally practised. See, for example, Goodman and Gilman, *The Pharmacological Basis of Therapeutics,* 1299 (7th Edition, 1985). The specific dosage utilised will depend upon the condition being treated, the state of the subject, the route of administration and other well known factors as indicated above.

The production of a pharmaceutical composition for the treatment of the therapeutic indications herein described (for convenience hereafter referred to as the "active compounds") are typically admixed with one or more pharmaceutically or veterinarially acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, optical, buccal (for example, sublingual), parenteral (for example, subcutaneous, intramuscular, intradermal, or intravenous) and transdermal administration, although the most suitable route in any given case will depend on the nature and severity of the condition being treated and on the nature of the particular active compound which is being used.

Formulation suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and are administered at a rate of 0.1 ml/minute/kg.

Formulations suitable for rectal administration are preferably presented as unit dose suppositories. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vaseline, lanoline, polyethylene glycols, alcohols, and combination of two or more thereof. The active compound is generally present at a concentration of from 0.1% to 0.5% w/w, for example, from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound.

Formulations suitable for transdermal administration may also be delivered by iontophoresis (see, for example, *Pharmaceutical Research* 3 (6), 318 (1986)) and typically take the form of an optionally buffered aqueous solution of the active compound. Suitable formulations comprise citrate or bis/tris buffer (pH 6) or ethanol/water and contain from 0.1 M to 0.2 M active ingredient.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Compounds of the present invention have potent antioxidant activity and thus find wide application in pharmaceutical and veterinary uses, in cosmetics such as skin creams to prevent skin ageing, in sun screens, in foods, health drinks, shampoos, and the like.

It has surprisingly been found that compounds of the formula I interact synergistically with vitamin E to protect lipids, proteins and other biological molecules from oxidation. Accordingly, a further aspect of this invention provides a composition comprising one or more compounds of the formula I, vitamin E, and optionally a pharmaceutically, veterinarially or cosmetically acceptable carriers and/or excipients.

Therapeutic methods, uses and compositions may be for administration to humans or animals, such as companion and domestic animals (such as dogs and cats), birds (such as chickens, turkeys, ducks), livestock animals (such as cattle, sheep, pigs and goats) and the like.

Compounds of the formula I may be prepared as follows:

A. Hydrogenation of daidzein, geniestein or derivatives thereof using palladium on calcium carbonate, as follows

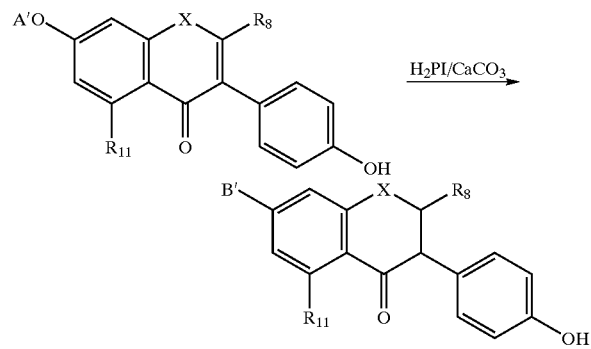

where A' is H or $R_1$ where $R_1$ is as previously defined and $R_8$ and $R_{11}$ and X are as previously defined. Compounds 2, 3, 4, 5, 6 and 7 may be produced by this method. Compounds 5 to 7 are enol forms of compounds 2 to 4.

B. Reduction of daidzein and daidzein derivatives with sodium borohydride as follows:

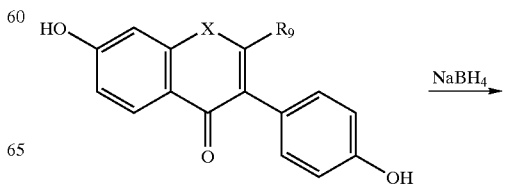

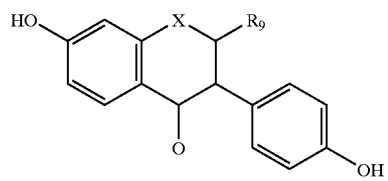

where $R_9$, and X are as previously defined. Compound 8 may be produced by this method.

C. Hydrogenation of daidzein and diadzein derivatives using palladium on charcoal as a catalyst.

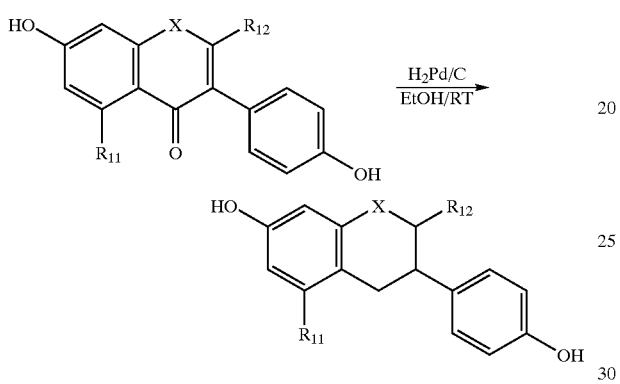

where $R_{11}$ and $R_{12}$ are as previously defined. Compound 10 may be produced by this method.

D. Acylation or resorcinol or derivatives thereof, followed by dehydrogenation with lithium bromide

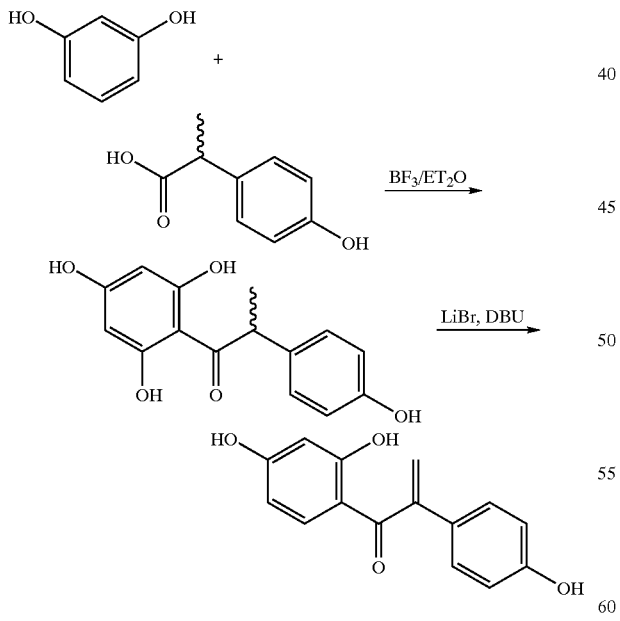

Compounds 11 and 14 may be produced by this method. Compound 12 may be produced in a similar manner.

E. Acylation of 1, 3 and 5 trisubstituted benze with 4-hydroxyphenyl isopropyl acid or derivatives thereof

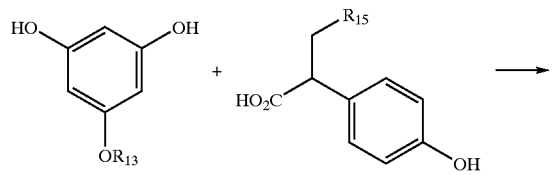

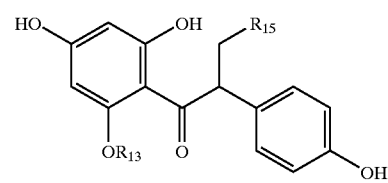

or

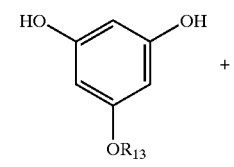

+

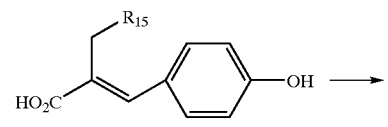

where $R_{13}$ and $R_{15}$ are as previsouly defined. Compounds 15 and 16 may be produced by this method.

F. Compounds of the formulae 17, 18 and 19 may be prepared according to the following reaction schemes.

(i)

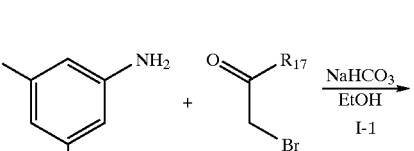

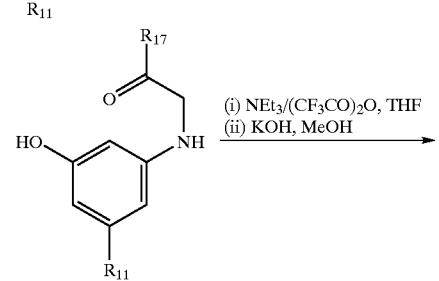

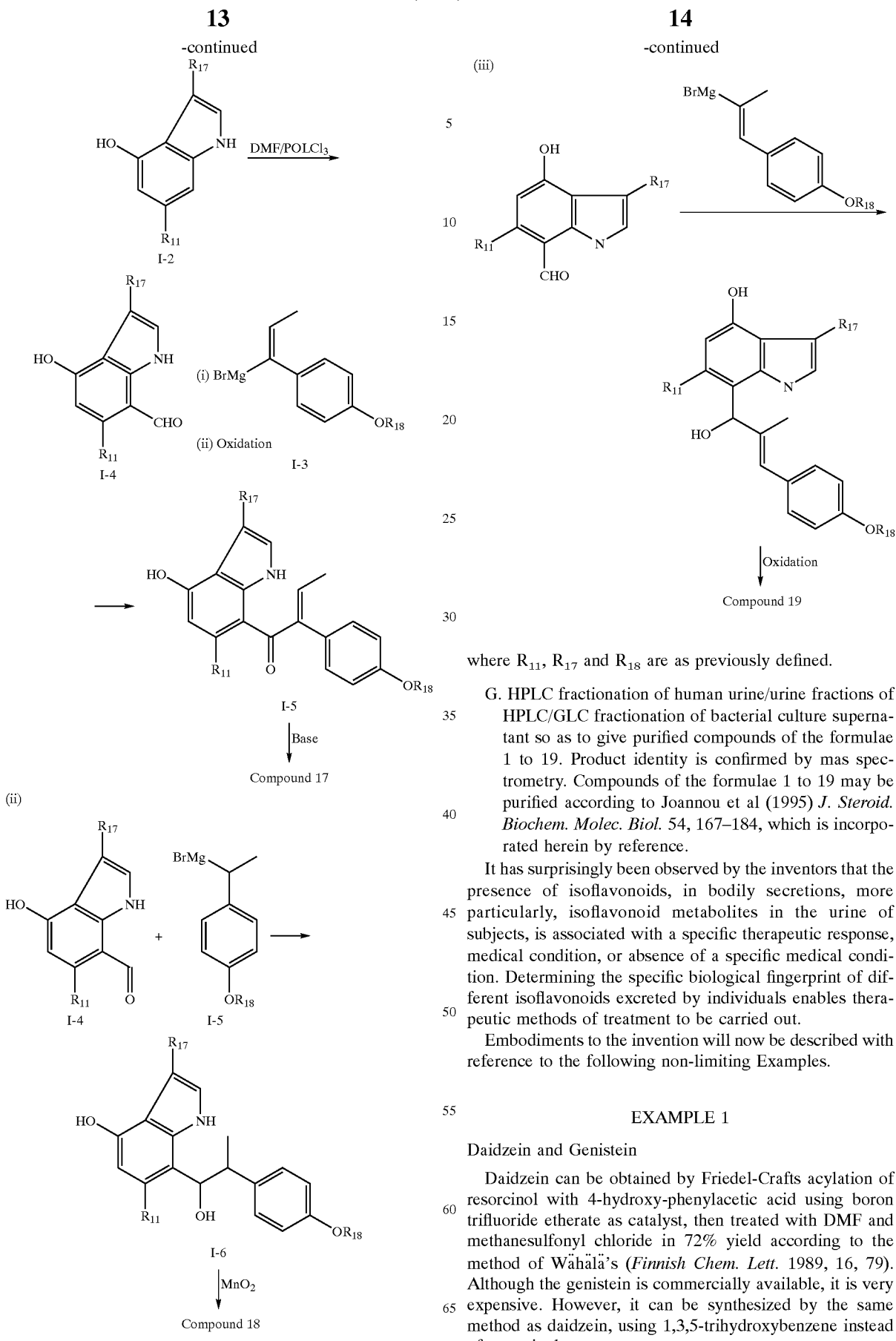

where $R_{11}$, $R_{17}$ and $R_{18}$ are as previously defined.

G. HPLC fractionation of human urine/urine fractions of HPLC/GLC fractionation of bacterial culture supernatant so as to give purified compounds of the formulae 1 to 19. Product identity is confirmed by mas spectrometry. Compounds of the formulae 1 to 19 may be purified according to Joannou et al (1995) *J. Steroid. Biochem. Molec. Biol.* 54, 167–184, which is incorporated herein by reference.

It has surprisingly been observed by the inventors that the presence of isoflavonoids, in bodily secretions, more particularly, isoflavonoid metabolites in the urine of subjects, is associated with a specific therapeutic response, medical condition, or absence of a specific medical condition. Determining the specific biological fingerprint of different isoflavonoids excreted by individuals enables therapeutic methods of treatment to be carried out.

Embodiments to the invention will now be described with reference to the following non-limiting Examples.

EXAMPLE 1

Daidzein and Genistein

Daidzein can be obtained by Friedel-Crafts acylation of resorcinol with 4-hydroxy-phenylacetic acid using boron trifluoride etherate as catalyst, then treated with DMF and methanesulfonyl chloride in 72% yield according to the method of Wähälä's (*Finnish Chem. Lett.* 1989, 16, 79). Although the genistein is commercially available, it is very expensive. However, it can be synthesized by the same method as daidzein, using 1,3,5-trihydroxybenzene instead of resorcinol.

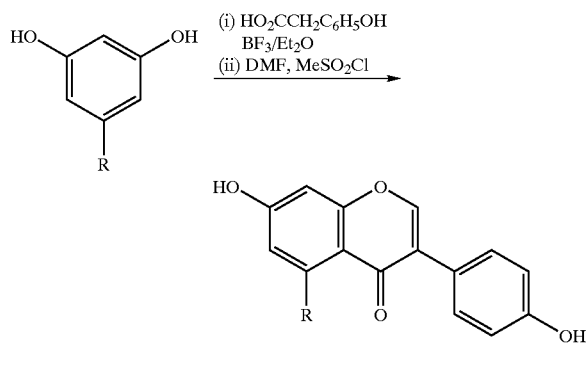

Where R is H the product is daidzein, when OH, genistein.

Dihydrodaidzein and Dihydrogenistein (Compounds 2 and 3 Respectively)

Hydrogenation of daidzein and genistein using palladium on calcium carbonate as a catalyst gives dihydrodaidzein and dihydrogenistein in good yield.

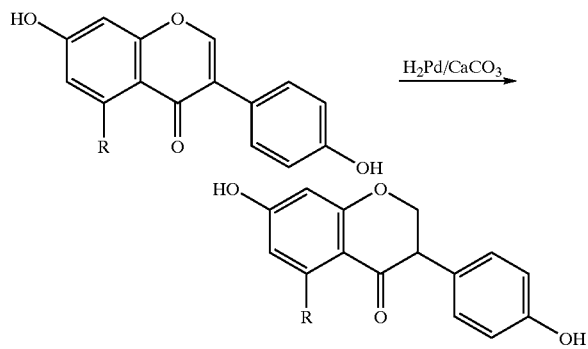

Where R is H the product is dihydrodaidzein, when OH, dihydrogenistein.

Tetrahydrodaidzein (Compound 8)

Reduction of daidzein with sodium borohydride gives the title compound.

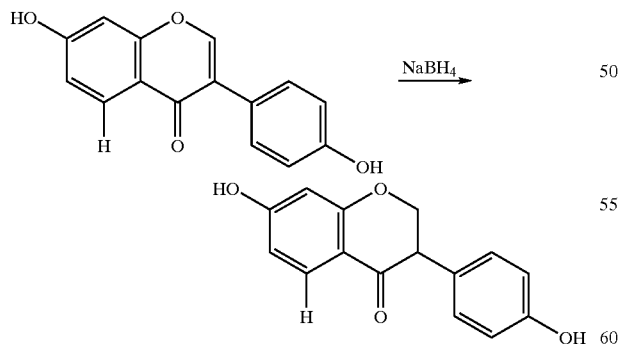

Equol Derivatives (Compound 10)

Equol derivatives are obtained from hydrogenation of daidzein derivatives using palladium on charcoal as a catalyst (*Finnish Chem Lett.* 1989, 16, 79).

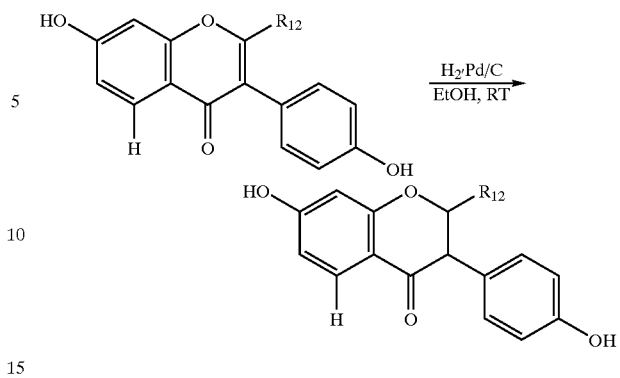

6-hydroxy-O-demethylangolensin (Compound 14)

4-hydroxyphenylisopropyl acid is acylated wtih 1,3,5-trihydroxybenzene to give the title compound.

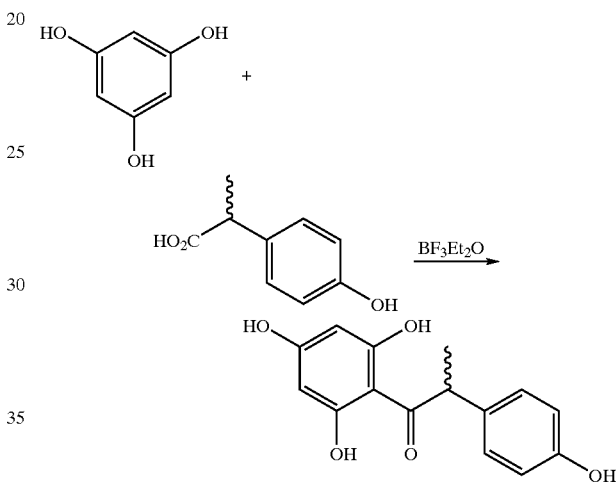

2-dehydro-O-demethylangolensin (Compound 11)

The title compound is obtained by acylation of resorcinol then dehydrogenation as shown below.

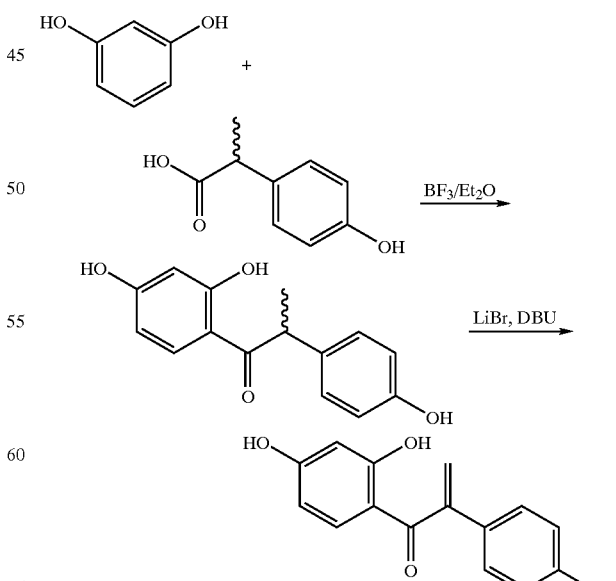

Compounds of the formulae 17, 18 and 19 are prepared as follows:

Compound 17

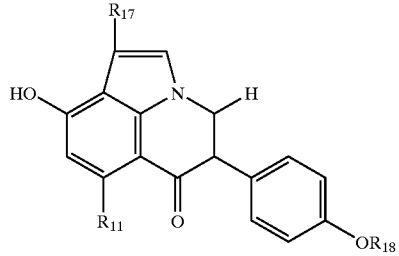

Compounds of the formula 17 are prepared according to the following reaction scheme

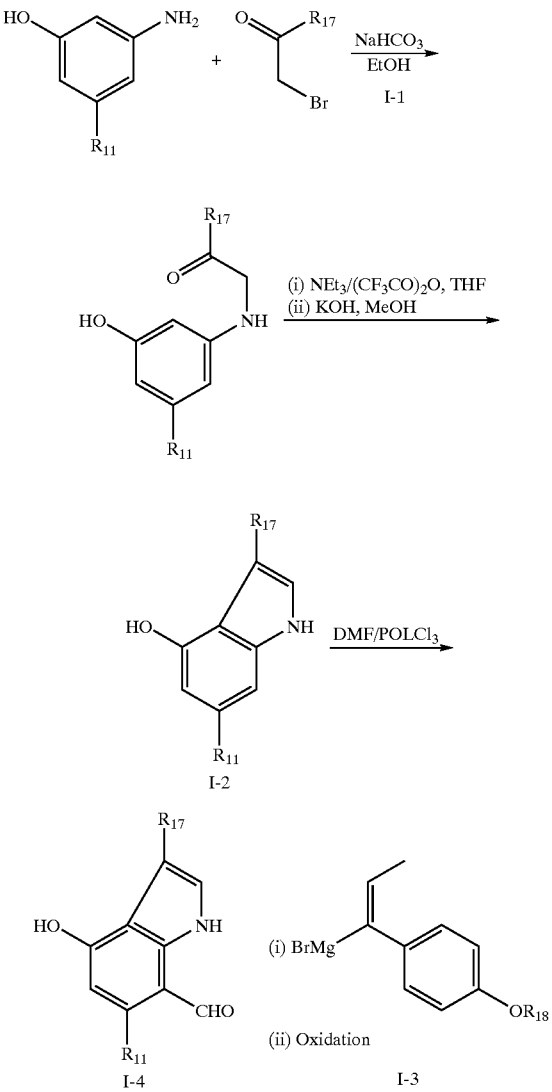

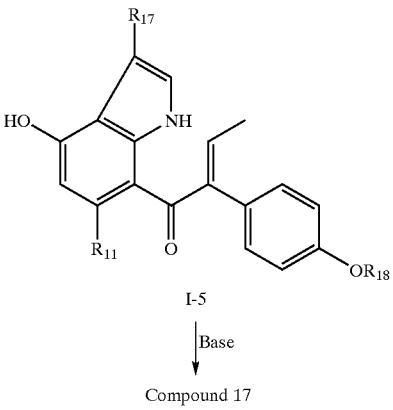

where $R_{11}$, $R_{17}$ and $R_{18}$ are as previously defined.

Indole I-2 is prepared as shown above according to the method of Black et al (*Aust. J. Chem.* 33 (1980) pages 343–350) which is incoporated herein by reference.

Indole I-4 is obtained by the Vilsmeier reaction. Electrophilic attack at 7-C position is preferred over that at 2-C position when there is an electron withdrawing group at the 3-C position. Nucleophilic addition of aldehyde with a Grignard reagent I-3 gives the secondary alcohol which on oxidation with $MnO_2$ will give the ketone I-5 and in mild base compounds of the formula 17.

Compound 18

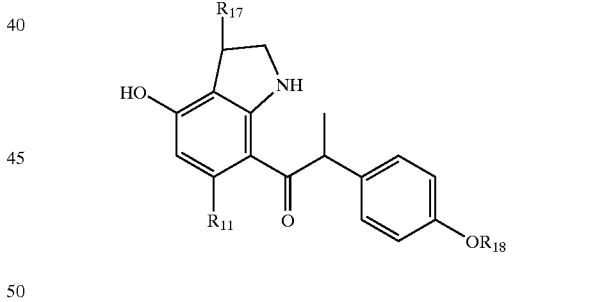

Compounds of the formula 18 are prepared according to the following reaction scheme:

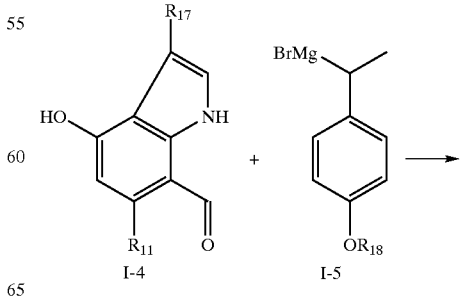

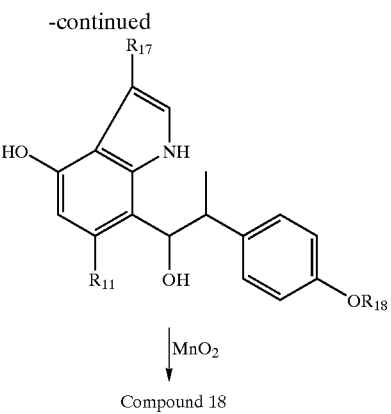

Compound 18

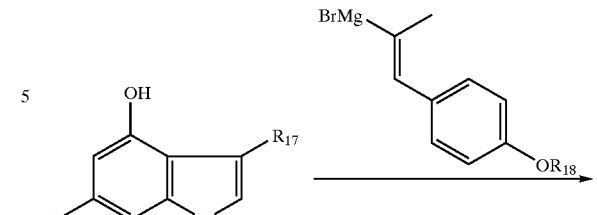

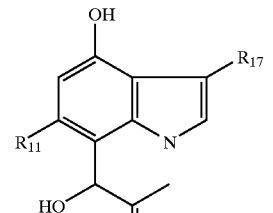

where $R_{24}$, $R_{25}$ and $R_{26}$ are as previously defined.

Nucleophilic addition of 7-aldehyde indole I-4 with Grignard reagent I-5 gives alcohol I-6 which on oxidation with $MnO_2$ gives compounds of the formula 18.

Compound 19

(19)

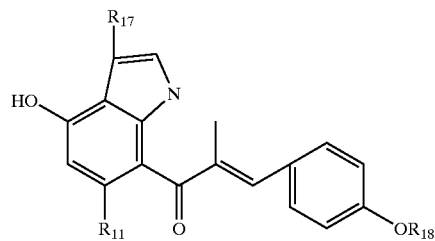

Compounds of the formula 19 are prepared according to the following reaction scheme:

Compound 19 where $R_{11}$, $R_{17}$ and $R_{18}$ are as previously defined.

EXAMPLE 2

Nitrogen and sulphur containin heterocyclic ring systems are synthesized according to the following reaction schemes:

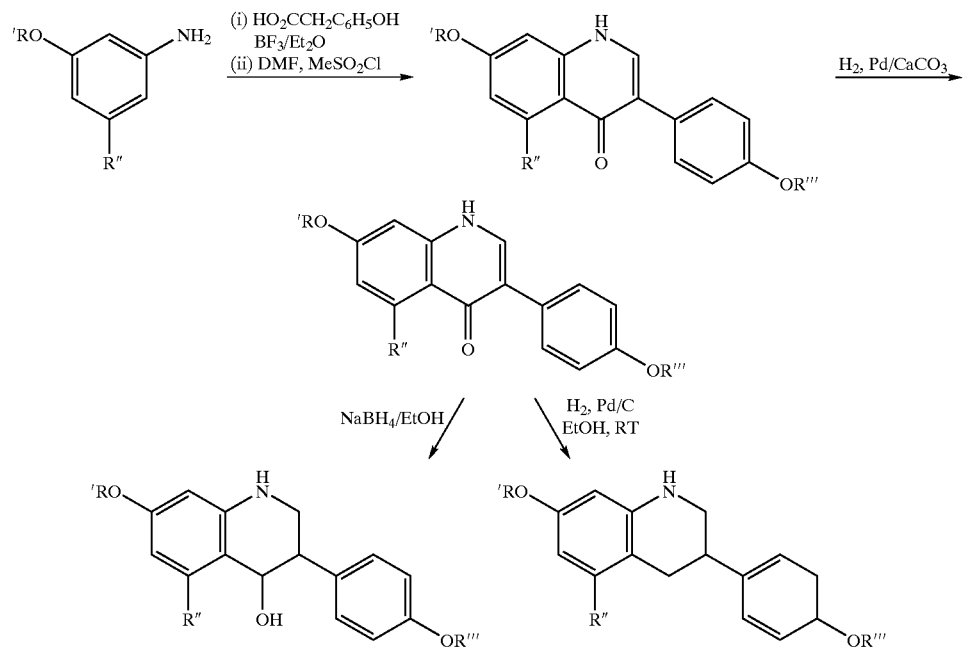

where R' is H or —OC$_{1-10}$ alkyl, R" is OH or OC$_{1-10}$ alkyl, and R''' is H or OC$_{1-10}$ alkyl.

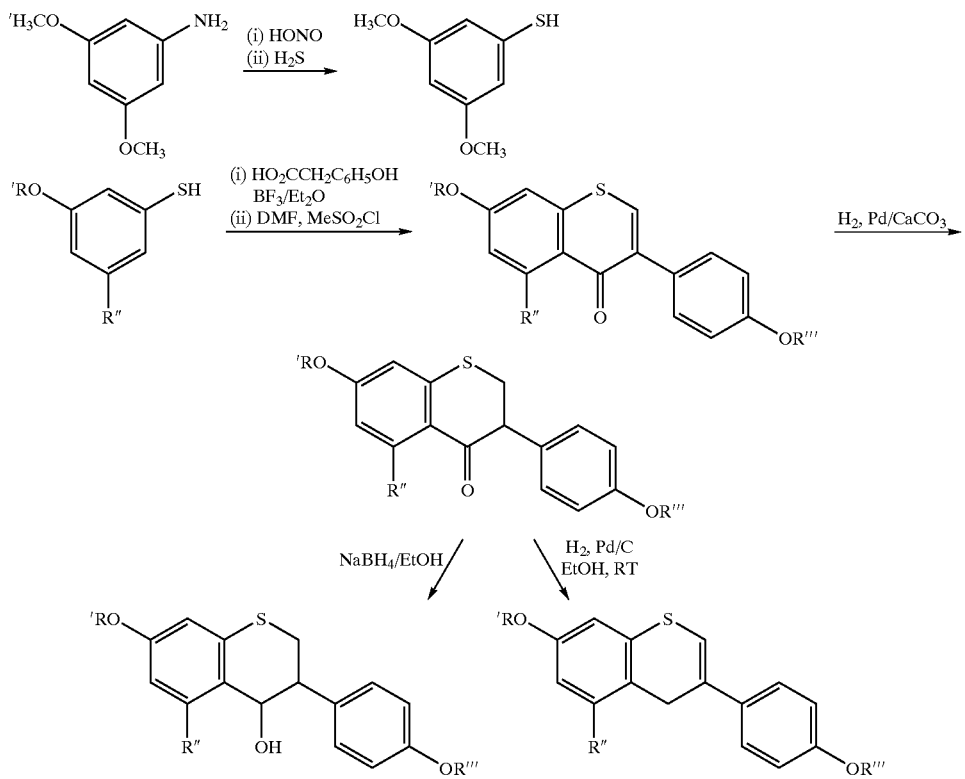

where R', R" and R''' is as previously defined.

EXAMPLE 3

1: Synthesis of ODMA (O-Desmethylangolensin 2,4,4'-trihydroxyphenyl-α-methyldesoxybenzoin). Compound 13

1.1: 2-(p-Methoxyphenyl)propionic acid

A mixture of p-methoxypropiophenone (2.39 g, 14.5 mmol), 90% lead(IV)acetate (6.45 g, 14.5 mmol), triethylorthoformate (15 ml) and 70% perchloric acid (1.2 ml, 29 mmol) was heated to 55° C. for 18 h. The mixture was cooled and the triethylorthoformate removed under reduced pressure. The residue was dissolved in CHCl$_3$ and the remaining precipitate filtered off and discarded. The CHCl$_3$ solution was then washed with water and evaporated to yield the crude ester. This crude ester product was dissolved in a 10% KOH 1:1 water:methanol solution, which was then refluxed for 3 h. After cooling the methanol was evaporated under reduced pressure and the aqueous solution washed with diethylether (3×25 ml). The aqueous solution was acidified with 2N H$_2$SO$_4$, then washed again with diethylether (3×25 ml). The combined fractions from the second ether wash were dried (Na$_2$SO$_4$) and evaporated to give the propionic acid (1.66 g, 63%).

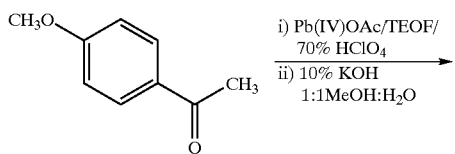

1.2: 2,4,4'-Trimethoxy-α-methyldesoxybenzoin 2-(p-Methoxyphenyl)propionic acid (0.39 g, 4 mmol) and 1,3-dimethoxybenzene (0.5 g, 0.5 ml, 4 mmol) were mixed in polyphosphoric acid (PPA) (10 g) and the reaction mixture was mechanically stirred at 75° C. for 5 h. The reaction mixture was then allowed to cool to room temperature and mechanically stirred for a further 12 h. The reaction was then quenched with ice water and the product extracted with CHCl$_3$ (3×25 ml). The CHCl$_3$ layer was dried (Na$_2$SO$_4$) and the solvent removed under reduced pressure. The residual crude product was purified by silica gel column chromatography (eluent 7:2 CH$_2$Cl$_2$:EtOAc) to give the pure 2,4,4'-trimethoxy-α-methyldesoxybenzoin (0.68 g, 58%)

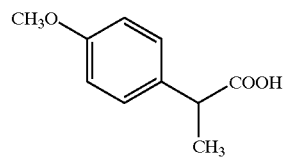

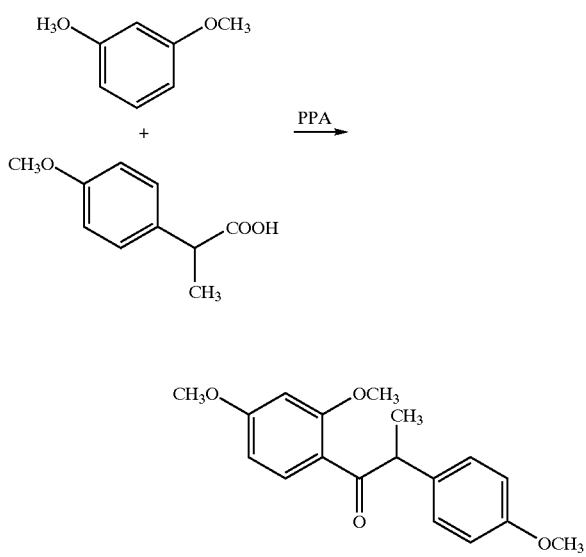

1.3 2,4,4'-Trihydroxyphenyl-α-methyldesoxybenzoin (O-Desmethylangolensin or O-DMA)

2,4,4'-Trimethoxy-α-methyldesoxybenzoin (0.312 g 1.04 mmol) was dissolved in dry CH₂Cl₂ (10 ml). To this solution 5 equivalents of 10M BBr₃ in hexane (1.3 g, 5.2 ml, 5.2 mmol) was added slowly and the reaction mixture allowed to stir under N₂ at room temperature for 6 days. Reaction was quenched with ice/water and after stirring for 1 h the product was extracted with diethylether (3×25 ml). The ether layer was dried (Na₂SO₄) and the solvent removed under reduced pressure. The residual crude product was purified by silica gel column chromatography (eluent 7:1 CH₂Cl₂:EtOAc) to give the pure 2,4,4'-trihydroxyphenyl-α-methyldesoxybenzoin (0.68 g, 58%)

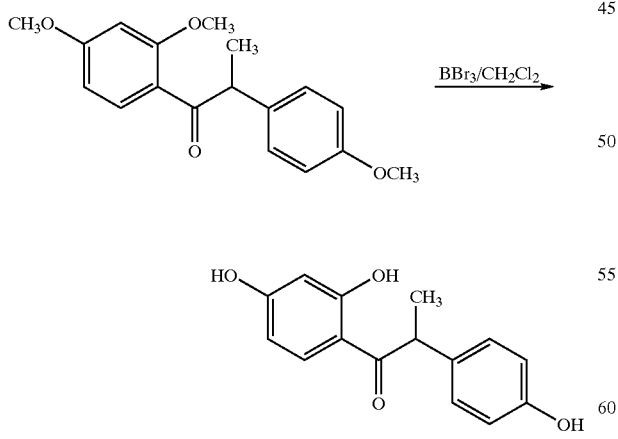

2: Synthesis of 4'methoxy 6OH-ODMA (4'methoxy6-OH-O-Desmethylangolensin 2,4,6,4'-tetrahydroxyphenyl-α-methyldesoxybenzoin)

2.1: Use of POCl₃ with Phloroglucinol and the p-methoxy phenyl propionic acid 2-(p-Methoxyphenyl)propionic acid (0.1 g, 0.55 mmol) and 1.1 equlivalents of 1,3,5-trihyroxybenzene (Phloroglucinol) (0.077 g, 0.61 mmol) were dissolved in dry tetrahydrofuran (THF) (2 ml). Freashly distilled POCl₃ (1.0 ml) was added to the solution and the reaction mixture was allowed to stir at room temperature for 4 days. The reaction was then quenched with ice water and the product extracted with diethylether (3×10 ml). The ether layer was dried (Na₂SO₄) and the solvent removed under reduced pressure. The residual crude product was purified by silica gel column chromatography (eluent 7:2 CH₂Cl₂:EtOAc) to give two products namely, the ester (1) and the desired 4'methoxy-6-OH-ODMA (2).

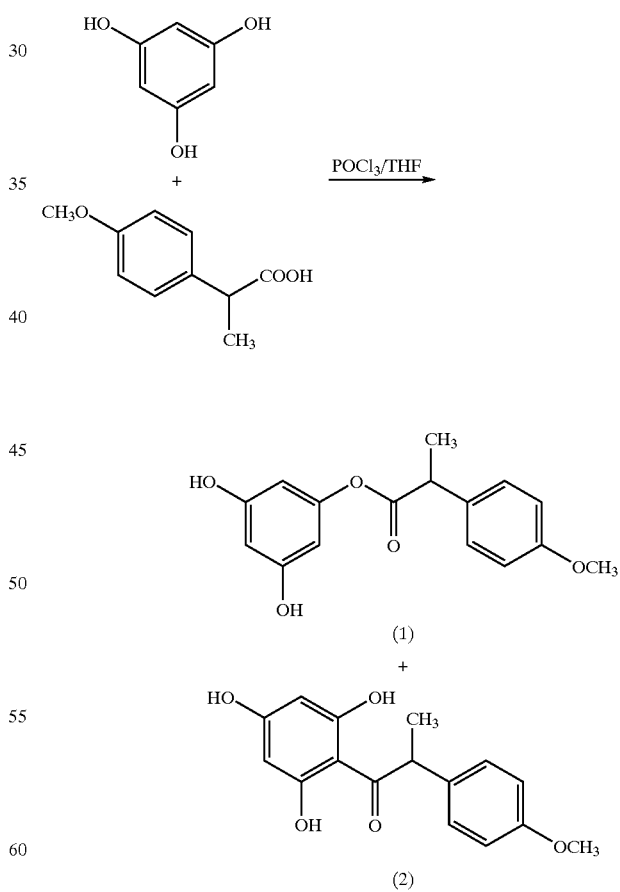

3: Synthesis of Dihydrodaidzein (Compound 1)
3.1 Synthesis of Daidzein

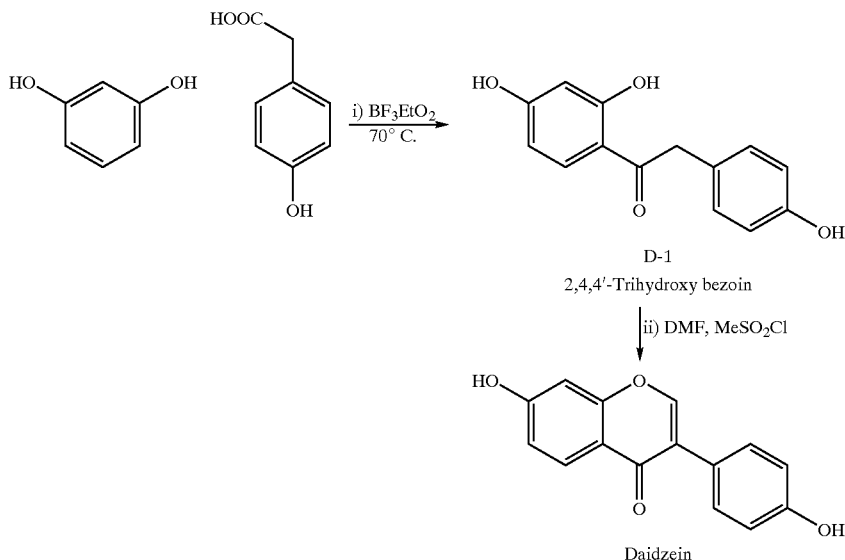

Resorcinol (29 mmol) and 4 hydroxyphenyl acetic acid (29 mmol) were dissolved into freshly distilled borontrifluoride etherate (20 mol eq) under nitrogen. The resulting mixture was stirred and heated at 70° C. for overnight. The reaction was monitored by TLC(80% Et2O/Hexane). The resulting mixture was cooled down at room temperature, then N,N-dimthylformamide (46.2 mL) was added dropwise. The mixture was again heated up at 50° C. for 30 minutes, then methanesulphonyl chloride (7 mL in 10 mL DMF) was added dropwise and the resulting mixture was heated at 60–70° C. until LC (80% $Et_2O$/Hexane) shown that the reaction was almost finished, about 10 hours. After cooling down at room temperature, the mixture was poured into 400 mL ice-cold water. The precipitate was filtered. The filtrate was collected and dried. The cure product was recrystallised in 94% ethanol (aq) and gave a quite pure daidzein (3 g) in 44% yield.

3-2 Synthesis of dihydrodaidzein

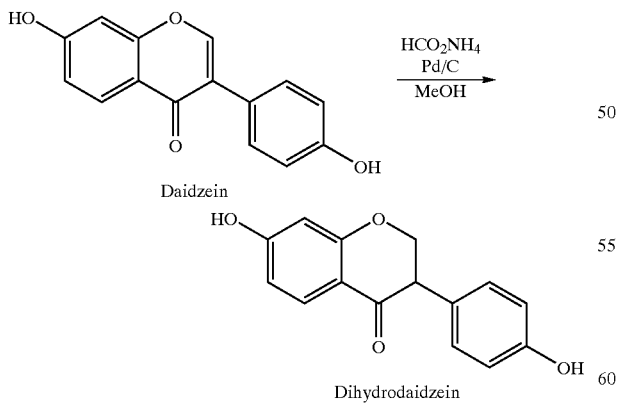

To a solution of daidzein (0.657 g, 2.58 mmol) in methanol (60 mL) was added 10% Pd/C (0.657 g) carefully, following by ammonium formate (0.652 g, 10.3 mmol). The mixture was heated up to 50–60° C. and stirred for one hour. The reaction was monitored by TLC ($CH_2Cl_2$/EtOAc=7:2 or 70% $Et_2O$/Hexane) and GC. After the reaction complete, the Pd/C was filtered and the filtrate was concentrated, which gave a crude product (0.558 g) of dihydrodaidzein as the major product and the trans/cis isomers of tetrahydrodaidzein as the minor products. The dihydrodaidzein was purified by standard procedures.

Other methods to provide dihydrodaidzein may be used such as that of Jain,A. C. and Mehta, A., J. Chem. Soc. Perkin Trans. 1, 1986, 215.

4: Synthesis of the Tetrahydrodaidzein trans/cis isomers (Compound 8)

4-1 Synthesis of tetrahydrodaidzein trans/cis

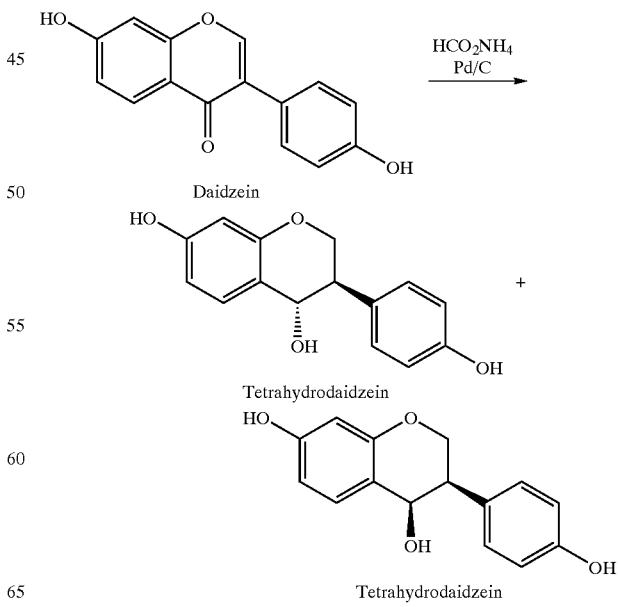

4-2 Synthesis of tetrahydrodaidzein trans/cis

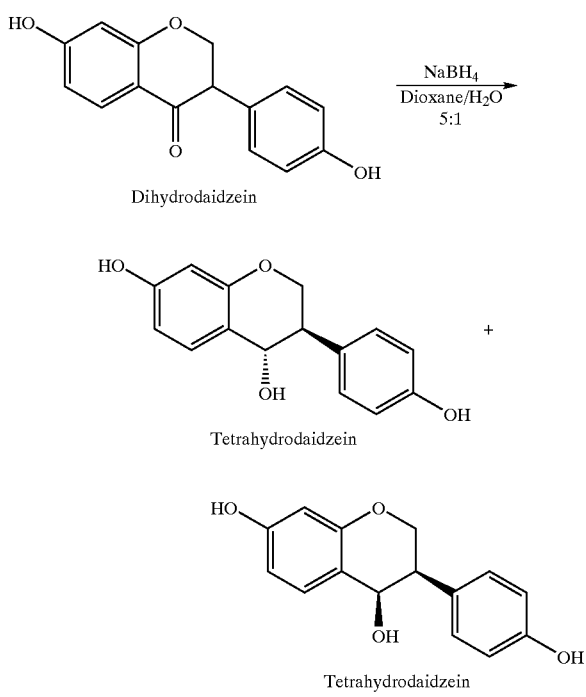

Dihydrodaidzein (0.001 g, 0.004 mmol) was dissolved in 200 L of dioxane and 40 L of water. Sodium boronhydride (0.002 g, 0.053 mmol) was added and the resulting mixture was stirred at room temperature for two hours. Excess sodium borohydride was then destroyed with a drop of acetic acid and the mixture was evaporated to dryness by nitrogen. The residue was extracted with EtOAc and organic layer was washed with water and then evaporated to dryness. Gas chromatography showed that most of dihydrodaidzein was converted to the tetrahydrodaidzein as confirmed by GC-MS [M+ 384. (G. E. Joannou, G. E. Kelly, A. Y. Reeder, M. Waring and C. Nelson. J.Steroid.Biochem. Molec. Biol. Vol.54, No 3/4, pp167–184,1995)]. Tetrahydrodaidzein was also synthesised by the reduction of dihydrodaidgein using sodium borohydride dioxane/H$_2$O (5:1) (Ref G. E. Joannou, G. E. Kelly, A. Y. Reeder, M. Waring and C. Nelson. J.Steroid.Biochem. Molec. Biol. Vol.54, No 3/4, pp167–184, 1995).

5: Synthesis of Dehydroequol (Compound 10)

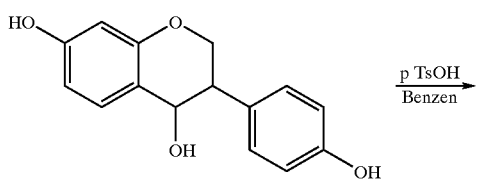

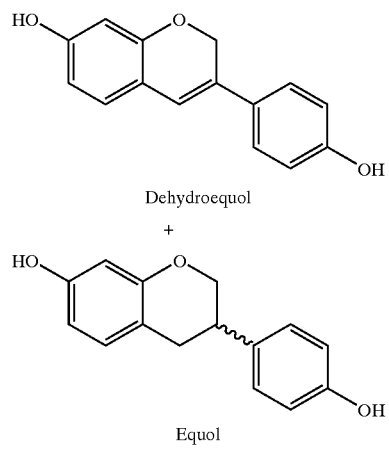

A mixture of tetrahydrodaidzein (0.02336 g) was suspended in dry benzene (5 mL) and p-toluenesulfonic acid (0.0487 g) was added to the reaction. The resulting mixture was heated up 95° C. for 35 min then the benzene was evaporated and the crude product was purified by the HPLC (MeOH/H2O=60:40) and gave dehydroequol and equol. The dehydroequol was confirmed by H NMR, GS-MS and high resolution MS.

6: Synthesis of Dihydrogenistein (Compounds 2 and 5)

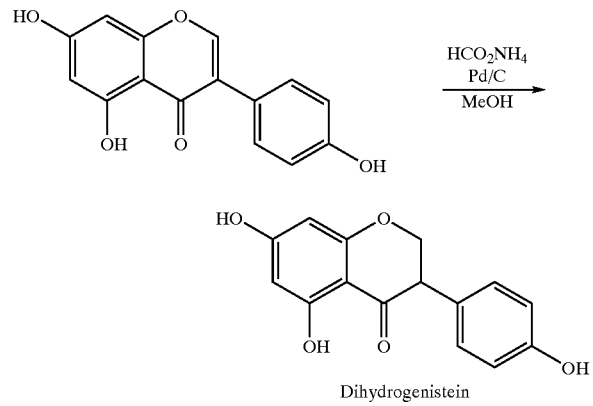

Genistein (Sigma, 0.0023 g, 0.0085 mmol) was dissolved in EtOH (2 mL) and 10% Pd/C (0.0023 g) and ammonium formate (0.0027 g, 0.043 mmol) were added to the solution with stirring. The resulting mixture was stirred overnight. GC showed that all the starting material was coverted to dihydrogenistein as confirmed by GC, GC-MS and NMR data. The reduction product was purified by the HPLC.

EXAMPLE 4

The urine of volunteers is screened by way of gas chromatography-mass spectrometry (GC-MS) as described by Kelly et al in *Clinica Chemica Act* (1993) 9–22, which is herein incorporated by reference). Those individuals whose urine contained greater than 0.5 μm and generally between 2.5 to 50 μm or more are selected for further study. Faecal samples were obtained from those individuals and microbial cultures made using standard faecal culture conditions. Microbial cultures which secrete the compounds of interest are detected by way of GC-MS. Organisms which secrete at least 50 μg of each of the compounds 1 through 19 were isolated. These organisms are used in microbial fermentation to produce compounds of the formulae 1 through 19. Where the organisms are selected from one of the classes Lactobacilli, *Clostridium perfringens,* Bacteroids, *Candida albicans* and other yeasts, *Anaerobic cocci,* Ruminococcus, Eubacterium, Peptostreptococcus, Clostridium, Bifidobacteria, Peptococcus, Streptococcus and/or *Anaerobic streptococci,* Gram-negative facultative bacteria, Fusobacterium they may be used directly in food compositions such as dairy formulations so as to provide compounds of the formulae 1 to 19.

EXAMPLE 5

Therapeutic formulations were prepared by admixing compounds of the formulae 1 to 19 with a soy flour base (defatted soy flour available from Edible Enhanced Protein St Marys, Australia).

A range of pharmaceutical formulations is prepared comprising between 40 mg and 200 mg of active compound to a dosage formed.

For the purposes of this example, gelatin capsules and tablets containing 200 mg of each of the active compounds 1 to 19 are prepared in the soy flour base referred to above, or in a cholesterol free yoghurt base.

EXAMPLE 6

A. Treatment of Vascular Conditions—Menopausal Syndrome, Hot Flushes, Hypertension, Atherosclerosis and Male Impotency Vascular reactivity studies using rat aortic rings is generally regarded as directly predictive of biological effects of candidate compounds in the treatment of the above conditions (Karapapanis, S. et al (1994) *Heptology,* 20, 6, 1516–1521). The inhibitory effect on restrictor responses in the aortic ring is measured in the presence of the vasoconstrictor noradrenaline according to the procedure of Karapapanis (supra). Dihydrodaidzein (Compound 1), dihydrogenestein (Compounds 2 and 5), tetrahydrodaidzein (Compound 8), ODMA (Compound 13) and equol (Compound 10) all exhibit potent inhibitory effects on responses to noradrenaline, that is, they inhibited vasoconstrictor responses.

Subsequent clinical studies are shown to demonstrate therapeutic benefits in the treatment of the above conditions using these compounds.

B. Hormone Responsive Cancer Treatment—Treatment of Hormone Related Cancers Including Breast, Ovarian, Testicular, Uterine, Endometrial and Prostatic Cancer The activity of compounds of the present invention in inhibiting the growth of hormone responsive cancer cells were tested using the well characterised human responsive cancer cell lines K562 and HL60. The anti-cancer screening assay measured inhibition of cell proliferation which results in terminal differential cell death. Cell death is due to either apoptosis or necrosis ODMA (Compound 13) and equol (Compound 10) or potent inhibitors of growth of cell lines K563 and HL60, this result being therefore directly predictive that these compounds will inhibit the growth of hormone related cancers such as those mentioned above. Tetrahydrodaidzein (Compound 8) showed strong inhibition of cell line HL60.

Subsequent clinical studies are shown to demonstrate therapeutic benefits in the treatment of the above conditions using these compounds.

C. Antioxidant Studies—Relevant to the Treatment of Cancer; Conditions Associated with Oxidation of Cholesterol Such as Atherosclerotic Vascular Disease; Myocardial Infarction, Stroke, Heart Disease; Arthritis and Cataracts Many studies have shown that compounds having antioxidant activity are useful therapeutics in the treatment of the above conditions (see for exampel McLaughlan et al (1995) *Biochem; Soc. Trans.* 23 (2) 2575; and van't Veer et al (1996) *Cander Epidemiol Biomarkers Prev.* 5 (6) 441–7)

Compounds according to this invention have antioxidant activity.

Tetrahydrodaidzein (Compound 8) and dehydroequol (Compound 10) are highly effective antioxidants. The following tests in relation to these compounds are carried out:

1. LDL Antioxidation Test—This test measures the ability of a compound to directly scavenge free radicals or to chelate transition metals. The longer the lag time, the more active the compound as an antioxidant under these conditions compared to ascorbate as a positive control. These tests were carried out according to the procedure of Esterbauer et al *Free. Rad. Res. Coms.* (1989) 6, 67–75. Briefly, LDL (0.25 mg/ml) is incubated with 10 μm active compound in the presence of 4 μm $Cu^{++}$, and LDL was assayed for oxidation by HPLC analysis. Results are as follows:

| Sample | Lag Times - min | % Increase Over Control |
|---|---|---|
| Control | 20 | |
| Ascorbate | 50 | 150 |
| Tetrahydrodaidzein | >140 | >600 |
| Dehydroequol | >140 | >600 |

This significant finding shows that tetrahydrodaizein and dehydroequol are extremely potent antioxidants and therefore may be regarded as effective therapeutics in the treatment of cancer, myocardial infarction, stroke, arthritis, sunlight induced skin damage cataracts, and other conditions resulting from oxidative damage.

2. Redox Test—This test measures the ability of a compound to prevent LDL lipid oxidation in the presence of vitamin E. The test is a physiological test, vitamin E (α-tocopherol) is present with LDL in the blood stream, and LDL oxidation is believed to be one of the major factors of the development of atherosclerosis. The lower values, the higher the redox activity. A high redox activity suggests that the compound is capable of interacting with the α-tocopherol in the LDL, perhaps by reducing the α-tocopheroxyl radical. The test indirectly assesses the ability of a compound to synergise with α-tocopherol in human LDL undergoing mild and chemically controlled oxidation. Oxidation is measured by the accumulation of cholesterylester hydroperoxides at a time point corresponding to 20% consumption of endogenous α-tocopherol. Butylated hydroxytoluene (BHT 10 μm) is used as a positive control. The redox index is measured by the relative extent of oxidation of LDL in the presence of the sample divided by the relative extent of oxidation in the absence of the test compounds. Active compounds give rise to low Redox Index. Tests were carried out according to Bowry, V. W. et al (1995) *J. Bio. Chem.* 270 (11) 5756–5763. Such tests show that compounds 1 to 19 synergistically interact with vitamin E to prevent oxidation of lipids, proteins, and other biological species.

By way of example dehydroequol (Compound 10) tested in this assay is shown to be a particularly superior antioxidant compared to a positive control antioxidant (BHT), the Redox Index for dehydroequol being 4.5±1.2, and that of BHT being 6.3.

The above test indicates that compounds 1 to 19, and particularly dehydroequol interacts synergistically with vitamin E to prevent oxidation. This is an important finding as vitamin E has previously been regarded as having opposing activities facilitation oxidation and decreasing oxidation of lipids and protein. Compositions containing one or more Compounds 1 to 19 and vitamin E may be used in the therapeutic treatment of cancer, myocardial infarction, stroke, arthritis, sunlight induced skin damage cataracts and other conditions responsive to treatment with antioxidants.

3. Synergism with α-tocopherol (TRAA)—This test directly assesses the ability of the test sample to attenuate α-tocopheroxyl radicals in cetyltrimethyl ammonium chloride (HTAC) or SDS micelles. Ascorbate is used as a positive control. Results are expressed as the relative rate constant of decay of α-tocopheroxyl radicals in the presence of the test sample divided by the relative rate constant of decay of α-tocopheroxyl radicals in the absence of the test sample. TRAA approaching unity is considered to have poor synergistic activity, whereas active compounds show large values because they eliminate the α-tocopheroxyl radicals immediately upon mixing.

The experiments were carried out according to Witting et al (1996) *J. Lipid Res.*, 37, 853–867. These studies show that Compounds 1 to 19, particularly dehydroequol (Compound 10), dihydrodaidzein and dihydrogenistein, interact synergistically with α-tocopherol.

4. LDL Receptor Studies—Treatment of atherosclerosis, myocardial infarction, stroke and hypertension. This will establish that compounds which up-regulate the LDL receptor, lead to decreased circulating LDL, and therefore reduces the prospect of atherosclerosis, myocardial infarction, stroke and hypertension. Using an assay according to Stephan Z. F. and Yurachek, E. C. (1993) *J. Lipid. Res.* 34, 325–330, it is shown that the compounds of the formulae 1 to 19 are effective in increasing LDL uptake into liver cells, this being directly predictive of decrease of circulating LDL in the human blood stream. ODMA and equol are shown to be particularly active in this respect.

EXAMPLE 7

Treatment of Acne

An 18 year old girl with acne since puberty, with no response to the contraceptive pill or any topical cream, and who declined the use of Roacutane on safety grounds, was administered a soy isoflavone extract containing genistein, daidzein, formononetin and Biochanin A which were converted into their metabolites namely compounds 1, 2, 5, 8, 10, 11, 13 and 14 as evidenced by urine analysis. 40 mg administered twice daily resulted in marked improvement of acne condition, colour, and general appearance within two weeks.

A 40 year old man with acne since puberty, with no response to any topical cream and who declined the use of Roacutane on safety grounds, as administered a soy isoflavone extract as described above. These isoflavones were converted to their metabolites namely compounds 1, 2, 5, 8, 10, 11, 13 and 14 as evidenced by urine analysis. Unexpectedly, he reported a dramatic improvement in his acne within two weeks, a change which hadn't been observed in over 20 years.

Subsequent clinical studies have shown to demonstrate therapeutic benefits in the treatment of acne utilising the above compounds.

Subsequent clinical studies are shown to demonstrate therapeutic benefits in the treatment of the above conditions.

EXAMPLE 8

A 67 year old man suffering from prostate cancer received a daily dosage of 16 mg of isoflavone extracts from clover which contained genistein, daidzein, formnononetin and biochanin A. After subsequent surgery for his prostate cancer condition the pathology report on the extracted prostate tissue showed an increased incidence of apoptosis (Stephens, F. O. (1997) *J. Aus. Med. Assoc.* 167, 3, 138–140). Analysis of this patient's urine showed the presence of aforementioned metabolites, this indicating that these compounds responsible for the amelioration of his condition in that the degenerative changes in the prostatectomy section, especially the apoptosis were indicative of androgen deprivation and typical of a response to estrogen therapy.

EXAMPLE 9

A patient group was studied comprising women who had a past history of breast cancer (who had been treated either by surgery or radiation, or both) and women who had a strong familial connection to breast cancer, that is, where their mothers or siblings had suffered from breast cancer. This study investigated whether compounds 1 through 19 administered transdermally each day through a skin patch could be used to prevent breast cancer or metastatic cancers following cancer therapy.

Patches were prepared that contained a lipophylic carrier cream which is readily absorbed through the skin. The cream comprised a glycerol cold cream which contained glycerin and peanut oil. A selected active compound from any one of compounds of the formulae 1 to 19 is mixed with the lipophylic cream such that each patch comprises 10 mg to 100 mg of active compound. The patch is applied to the skin each day and rapid absorption occurs. After two hours the patch is removed. Alternatively, the patch may be left on for a greater part of each day.

Over a one year study period it is found that this high risk group does not show any evidence of breast cancer or other metastatic cancer.

The effectiveness of this treatment is shown in another study of a similar group of high risk patients. Compounds 11, 13 and 14 are transdermally administered to patients in the same manner and amount as above. The same beneficial results are observed over a six month trial period.

EXAMPLE 10

A study of a group of patients suffering from benign prostatic hypertrophy (BPH) and prostatic cancer of various grades is carried out to determine the effect of administration of compounds of the formulae 1 to 19. The administration protocol was the same as for Example 3 involving daily administration of a gelatin capsule containing 200 mg of active compound. A significant decrease in the rate of production of relevant cancer markers (PSA, prostate specific antigen) is observed. Tumours are again shown to have regressed, or show no further growth. In another study a 45 year old male with BPH presented with urinary obstruction and frequency of urination. Upon taking 40 mg per day of a clover isoflavone containing extract became symptom free. Urine analysis showed the presence of the urinary metabolites described above.

A patient suffering from advanced bowel cancer is treated daily for three weeks with an intravenous infusion of 2 g of the compound of the formula 14 dissolved in sterile saline. The patient's pain and discomfort was significantly reduced, and reduction in cancer markers is observed. Progression of the tumour is also arrested over the treatment period.

A second patient suffering from the same condition is treated in the same manner as the above patient with the exception that the 2 g dose of the active compound is administered by way of bolus injection. The results obtained were the same as those discussed in the above paragraph.

In a further series of experiments a group of patients suffering from terminal bowel cancer were treated by bolus daily injections (intravenous or intramuscular) of 2 g of a compound selected from one of the formulae 1 to 19. Over the test period there is shown to be a marked reduction in pain and discomfort. Tumour markers (carcino-embryonic antigen (CEA)) are reduced as evidenced by blood analysis and tumour spread decreased.

EXAMPLE 11

A study of patients suffering from male pattern baldness was carried out. Each of the subjects received a daily application to the scalp of an inert pharmaceutical gel containing 50 mg of active material. Over the one month study period there is observed a light down or stubble appearing on the treated area. This study indicates that the compounds are effective in the treatment of hair loss and with long term application should provide hair regeneration.

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claim is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

The claims defining the invention are as follows:
1. A method for the treatment or prophylaxis of a cancerous disease which comprises administering to a subject in need thereof a therapeutically effective amount of at least one compound of the formula I:

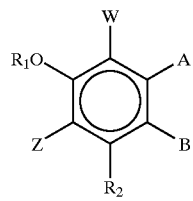

(I)

wherein

Z is H;

$R_1$ is H or $R_A CO$, where $R_A$ is $C_{1-10}$ alkyl or an amino acid;

$R_2$ is H, OH, or $OR_B$, where $R_B$ is an amino acid or $COR_A$, where $R_A$ is $C_{1-10}$ alkyl or an amino acid;

W is H; and A and B taken together form a six membered ring selected from

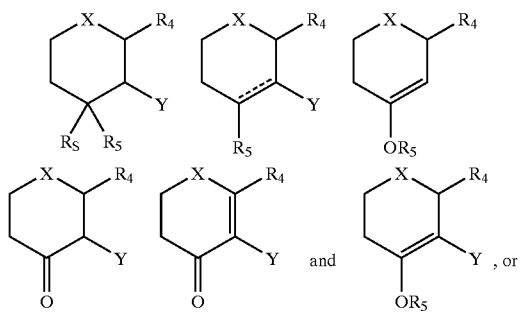

wherein $R_4$ is H, $COR_D$, $CO_2 R_C$, $COR_E$, COOH, $COR_C$, or $CONHR_E$, where $R_D$ is H, OH, $C_{1-10}$ alkyl or an amino acid, $R_C$ is $C_{1-10}$ alkyl, $R_B$ is H, $C_{1-10}$ alkyl or an amino acid, and $R_E$ is H, $C_{1-10}$ alkyl or an amino acid;

$R_5$ is H, $CO_2 R_C$, or $COR_C OR_E$, where $R_C$ is $C_{1-10}$ alkyl, and $R_E$ is H, $C_{1-10}$ alkyl or an amino acid, and with the proviso that where the two $R_5$ groups are attached to the same group they are identical or different;

X is O, N, or S; and

Y is

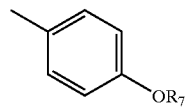

where $R_7$ is H, or $C_{1-10}$ alkyl, and with the provisos that compounds where $R_1$ and W are H, Z is H or $OCH_3$ and $R_2$ is H or OH, $R_4$ is COOH or $CO_2 R_C$ and $R_C$ is $C_2$ alkyl, A and B taken together are a six membered ring of the formula

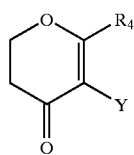

Y is

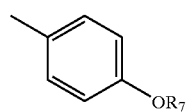

and

R$_7$ is H, and where

R$_1$ and W are H, Z is H, R$_2$ is OH,

A and B taken together are a six membered ring of the formula

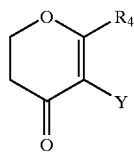

Y is

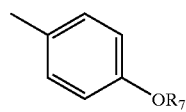

R$_4$ is COR$_D$ where R$_D$ is H, OH, C$_{1-10}$ alkyl or amino acid, and

R$_7$ is H, are excluded.

2. A method according to claim 1, wherein a therapeutically effective amount of at least one compound of the formula I is selected from

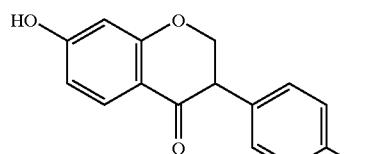
(1)

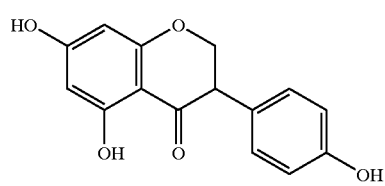
(2)

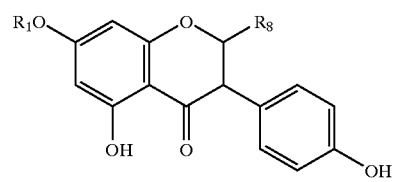
(3)

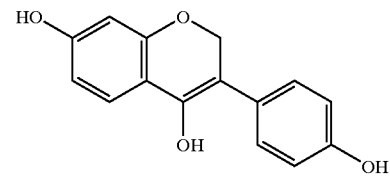
(4)

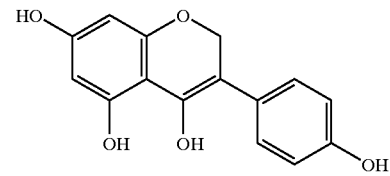
(5)

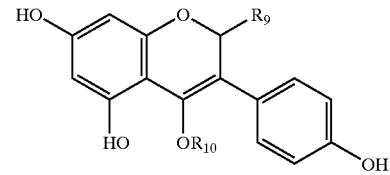
(6)

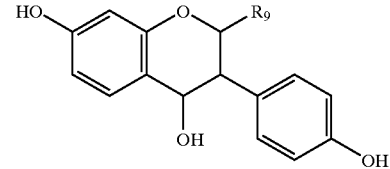
(7)

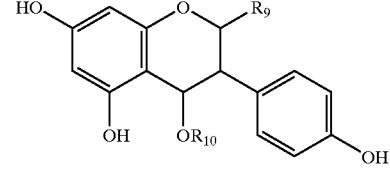
(8)

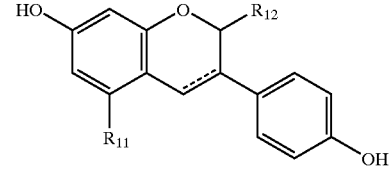
(9)

wherein

R$_1$ is R$_A$CO, where R$_A$ is C$_{1-10}$ alkyl or an amino acid,

R$_8$ is COR$_D$ where R$_D$ is H, OH, C$_{1-10}$ alkyl or an amino acid,

R$_9$ is R$_9$CO$_2$R$_C$ or COR$_E$ where R$_C$ is C$_{1-10}$ alkyl, and R$_E$ is H, OH, C$_{1-10}$ alkyl or an amino acid, R$_{10}$ is COR$_C$ or COR$_C$R$_E$ where R$_C$ is C$_{1-10}$ alkyl and R$_E$ is H, OH, C$_{1-10}$ alkyl or an amino acid, R$_{11}$ is H or OH, R$_{12}$ is H, COOH, CO$_2$R$_C$ where R$_C$ is C$_{1-10}$ alkyl, or CONHR$_E$ where R$_E$ is H, C$_{1-10}$ alkyl or an amino acid, and "---" represents either a single bond or double bond.

3. A method according to claim 2 wherein at least one compound of the formula 8 and 10 is administered to a subject in need thereof in need thereof together with a pharmaceutically acceptable carrier or excipient.

4. A method according to claim 1, wherein the cancerous disease is a hormone responsive cancer.

5. A method according to claim 1, wherein the cancerous disease is a metastatic cancer condition.

6. A method according to claim 1, wherein the treatment of prophylaxis is associated with cancer cell apoptosis.

7. A method according to claim 1, wherein the treatment or prophylaxis is associated with cancer necrosis.

8. A method according to claim 1, wherein the treatment or prophylaxis is associated with inhibition of cancer cell growth.

9. A method according to claim 1, wherein the cancerous disease is selected from breast cancer, uterine cancer, ovarian cancer, testicular cancer, bowel cancer, endometrial cancer, prostatic cancer, and leukemia.

10. A method according to claim 9, wherein the cancerous disease is breast cancer.

11. A method according to claim 10, which is a method for the treatment or prophylaxis of metastatic breast cancer.

12. A method according to claim 9, wherein the cancerous disease is ovarian cancer.

13. A method according to claim 9, wherein the cancerous disease is testicular cancer.

14. A method according to claim 9, wherein the cancerous disease is endometrial cancer.

15. A method according to claim 9, wherein the cancerous disease is prostatic cancer.

16. A method according to claim 9, wherein the cancerous disease is bowel cancer.

17. A method according to claim 1 wherein said at least one compound of the formula (I) is administered by way of oral, rectal, parenteral, transdermal, intradermal or topical administration.

18. A method according to claim 1 wherein said at least one compound of the formula (I) is administered at a daily dose of 0.1 mg to 2000 mg.

19. A method according to claim 18 wherein a daily dose of 50 mg to 500 mg is administered.

20. A method according to claim 1 wherein said at least one compound of the formula (I) is administered in association with a pharmaceutically acceptable carrier and/or excipient.

21. A method according to claim 1 wherein said at least one compound of the formula (I) is administered with vitamin E.

* * * * *

UNITED STATES PATENT AND TRADEMARK OFFICE
CERTIFICATE OF CORRECTION

PATENT NO. : 6,649,648 B1
DATED : November 18, 2003
INVENTOR(S) : Graham Edmund Kelly et al.

It is certified that error appears in the above-identified patent and that said Letters Patent is hereby corrected as shown below:

Column 34,
Line 25, please delete 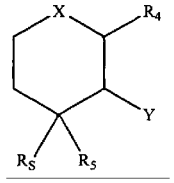 and in its place insert 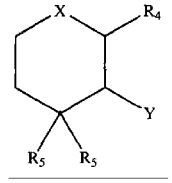

Line 41, please delete "$R_B$" and in its place insert -- $R_E$ --.

Column 36,
Line 67, please delete "8 and 10" and in its place insert -- 7 and 9 --.

Column 37,
Line 1, please delete "in need thereof in need thereof" and in its place insert -- in need thereof --.

Signed and Sealed this

Thirteenth Day of July, 2004

JON W. DUDAS
*Acting Director of the United States Patent and Trademark Office*